US011135177B2

(12) United States Patent
Birbara

(10) Patent No.: US 11,135,177 B2
(45) Date of Patent: Oct. 5, 2021

(54) METHODS OF MAKING AND USING COMPOSITIONS COMPRISING FLAVONOIDS

(71) Applicant: VIZURI HEALTH SCIENCES CONSUMER HEALTHCARE, INC., Bonita Springs, FL (US)

(72) Inventor: Philip J. Birbara, West Hartford, CT (US)

(73) Assignee: Vizuri Health Sciences Consumer Healthcare, Inc., Bonita Springs, FL (US)

(*) Notice: Subject to any disclaimer, the term of this patent is extended or adjusted under 35 U.S.C. 154(b) by 0 days.

(21) Appl. No.: 15/694,533

(22) Filed: Sep. 1, 2017

(65) Prior Publication Data

US 2018/0008553 A1 Jan. 11, 2018

Related U.S. Application Data

(62) Division of application No. 13/503,458, filed as application No. PCT/US2010/002821 on Oct. 22, 2010, now Pat. No. 9,889,098.

(60) Provisional application No. 61/253,857, filed on Oct. 22, 2009.

(51) Int. Cl.
| | | |
|---|---|---|
| A61K 9/70 | (2006.01) | |
| A61K 8/49 | (2006.01) | |
| A61K 9/00 | (2006.01) | |
| A61K 31/00 | (2006.01) | |
| A61K 31/353 | (2006.01) | |
| A61Q 19/00 | (2006.01) | |

(52) U.S. Cl.
CPC ............ *A61K 9/7023* (2013.01); *A61K 8/498* (2013.01); *A61K 9/0014* (2013.01); *A61K 31/00* (2013.01); *A61K 31/353* (2013.01); *A61Q 19/00* (2013.01); *A61K 2800/412* (2013.01); *A61K 2800/592* (2013.01); *A61K 2800/652* (2013.01)

(58) Field of Classification Search
None
See application file for complete search history.

(56) References Cited

U.S. PATENT DOCUMENTS

| | | | |
|---|---|---|---|
| 2,421,061 A | 5/1947 | Higby | |
| 2,442,110 A | 5/1948 | Baier | |
| 2,700,047 A | 1/1955 | Wilson | |
| 4,603,046 A | 7/1986 | Georgalas et al. | |
| 5,043,323 A | 8/1991 | Bombardelli et al. | |
| 6,099,825 A | 8/2000 | McShane et al. | |
| 6,409,996 B1 | 6/2002 | Plaschke | |
| 6,440,432 B1 | 8/2002 | Mukherjee et al. | |
| 6,814,959 B1 | 11/2004 | Müller et al. | |
| 6,890,561 B1 | 5/2005 | Blatt et al. | |
| 7,235,295 B2 | 6/2007 | Laurencin et al. | |
| 7,387,805 B2 | 6/2008 | Tsuzaki et al. | |
| 7,858,080 B2 | 12/2010 | Chung et al. | |
| 7,919,113 B2 | 4/2011 | Domb | |
| 8,637,569 B2 | 1/2014 | Birbara | |
| 9,730,953 B2 | 8/2017 | Birbara | |
| 2002/0054891 A1 | 5/2002 | Anderson et al. | |
| 2003/0119909 A1 | 6/2003 | Stanislaus | |
| 2004/0058983 A1 | 3/2004 | Vuorela et al. | |
| 2004/0081670 A1 | 4/2004 | Behnam | |
| 2004/0081675 A1* | 4/2004 | Wirth | A61K 8/498 424/401 |
| 2004/0191300 A1 | 9/2004 | Fecht et al. | |
| 2004/0220116 A1 | 11/2004 | Behnam | |
| 2005/0049291 A1 | 3/2005 | Kumar et al. | |
| 2005/0209313 A1 | 9/2005 | Wallace | |
| 2005/0281869 A1 | 12/2005 | Kruse et al. | |
| 2006/0040894 A1 | 2/2006 | Hunter et al. | |
| 2006/0078630 A1* | 4/2006 | Schempp | A61K 8/498 424/725 |
| 2006/0099270 A1 | 5/2006 | Friggeri et al. | |
| 2006/0257334 A1 | 11/2006 | Dahms et al. | |
| 2007/0003502 A1 | 1/2007 | Tanabe et al. | |
| 2007/0140984 A1 | 6/2007 | Kusano et al. | |
| 2008/0254188 A1 | 10/2008 | Borowy-Borowski et al. | |
| 2009/0082400 A1* | 3/2009 | Lee | A61K 31/453 514/326 |
| 2010/0047297 A1 | 2/2010 | Petersen | |
| 2010/0183524 A1 | 7/2010 | Zielinski et al. | |
| 2011/0223256 A1 | 9/2011 | Zhang et al. | |

(Continued)

FOREIGN PATENT DOCUMENTS

| | | |
|---|---|---|
| AU | 2011318580 | 1/2016 |
| AU | 2010308571 | 10/2016 |

(Continued)

OTHER PUBLICATIONS

CN101045072A Translation accessed from: https://patents.google.com/patent/CN101045072A/en?q=(apigenin)&q=(hydroxide)&before=priority:20090101&oq=(apigenin)+(hydroxide)+before:priority:20090101; accessed on Dec. 26, 2019; pp. 1-10 (Year: 2019).*
Abstract of Hertel et al., "Inhibitory effects of triterpenes and flavonoids on the enzymatic activity of haluronic acid-splitting enzymes," *Arch. Pharm.* (*Weinheim*), vol. 339, No. 6: 313-8 (2006).
Abstract of Liu et al., "Preparation of apigenin niosomes and properties investigation," *Journal of Shenyang Pharmaceutical University*, vol. 26, No. 6: 423-429 (2009).

(Continued)

*Primary Examiner* — Michael G. Hartley
*Assistant Examiner* — Lance W Rider
(74) *Attorney, Agent, or Firm* — Nixon & Vanderhye P.C.

(57) ABSTRACT

The subject invention relates to novel micoparticulate and soluble forms of flavonoids, and their synthesis. The invention also includes novel formulations of such flavonoids. Further, the invention includes novel methods of manufacturing the flavonoid formulations. The invention also relates to a wide variety of applications of the flavonoid formulations.

2 Claims, 11 Drawing Sheets

(56) References Cited

U.S. PATENT DOCUMENTS

| | | |
|---|---|---|
| 2012/0128777 A1 | 5/2012 | Keck et al. |
| 2012/0148567 A1 | 6/2012 | Kurisawa et al. |
| 2012/0213842 A1 | 8/2012 | Birbara |

FOREIGN PATENT DOCUMENTS

| | | | |
|---|---|---|---|
| CN | 1356327 | | 7/2002 |
| CN | 101045072 | A * | 10/2007 |
| CN | 101164536 | | 4/2008 |
| CN | 101518262 | | 9/2009 |
| CN | 1761450 | | 5/2010 |
| DE | 101 03 454 | | 8/2002 |
| DE | 101 29 973 | | 1/2003 |
| DE | 102 60 872 | | 7/2004 |
| EP | 0 179 583 | | 4/1986 |
| EP | 1 600 143 | | 11/2005 |
| EP | 1 731 134 | | 12/2006 |
| EP | 2 359 702 | | 8/2011 |
| JP | 10-101705 | | 4/1998 |
| JP | 2004-531530 | | 10/2004 |
| JP | 2005-521629 | | 7/2005 |
| JP | 2005-526785 | | 9/2005 |
| JP | 2007-197328 | | 8/2007 |
| JP | 5965319 | | 8/2016 |
| JP | 6105475 | | 3/2017 |
| KR | 10-2005-0102686 | | 10/2005 |
| KR | 10-1734424 | | 5/2017 |
| MX | 338211 | | 3/2016 |
| WO | WO 01/03652 | | 1/2001 |
| WO | WO 03/000191 | | 1/2003 |
| WO | WO 03/080024 | | 10/2003 |
| WO | WO 2006/020164 | | 2/2006 |
| WO | WO 2007/000193 | | 1/2007 |
| WO | WO 2007/006497 | | 1/2007 |
| WO | WO 2008/072954 | | 6/2008 |
| WO | WO 2008/101344 | | 8/2008 |
| WO | WO 2010/007252 | | 1/2010 |
| WO | WO 2010/062824 | | 6/2010 |
| WO | WO 2010/062835 | | 6/2010 |
| WO | WO 2010/121700 | | 10/2010 |
| WO | WO 2011/047227 | | 4/2011 |
| WO | WO 2011/089247 | | 7/2011 |
| WO | WO 2011/149854 | | 12/2011 |
| WO | WO 2012/003515 | | 1/2012 |

OTHER PUBLICATIONS

Blanco-Andujar et al., "Synthesis of nanoparticles for biomedical applications," Annu. Rep. prog. Chem., Sect. A, No. 106: 553-568 (2010).
Bowen, "Particle Size Distribution Measurement from Millimeters to Nanometers and from Rods to Platelets," Journal of Dispersion Science and Technology, vol. 23, No. 5: 631-662 (2002), Marcel Dekker, Inc., New York.
Brown et al., Hyaluronic acid: a unique topical vehicle for the localized delivery of drugs to the skin. JEADV (2005) 19, 308-318.
Casetti et al., "Topical application of solubilized Reseda luteola extract reduces ultraviolet B-induced inflammation in vivo," Journal of Photochemistry and Photobiology B: Biology, vol. 96: 260-265 (2009).
Chebil et al., "Solubility of Flavonoids in Organic Solvents", J. Chem. Eng. Data 52:1552-1556 (2007).
Chen et al., "A facile nanoaggregation strategy for oral delivery of hydrophobic drugs by utilizing acid-base neutralization reactions," Nanotechnology, vol. 19, No. 375104: 1-7 (2008).
Chen Ping et al. A Study on the Complex Reaction, Between Apigenin and Zinc. Journal of Food Science, vol. 29, 8, 151-154, Dec. 31, 2008.
Choi et al., "Influence of heat treatment on the antioxidant activities and polyphenolic compounds of Shiitake (Lentinus edodes) mushroom", Food Chemistry 99:381-387 (2006).

Engstrom et al., "Templated Open Floes of Nanorods for Enhanced Pulmonary Delivery with Pressurized Metered Dose Inhalers," Pharmaceutical Research, vol. 26, No. 1: 101-117 (Jan. 2009).
Iqbal et al., "Stabilization of sunflower oil by garlic extract during accelerated storage", Food Chemistry 100(1):246-254 (2007).
Kim et al., "Aqueous Solubility Enhancement of Some Flavones by Complexation with Cyclodextrins", Bull Korean Chem. Soc. 29:590-594 (2008).
Li et al., "Evaluation of Properties of Apigenin and [G-$^3$H]Apigenin and Analytic Method Development", Journal of Pharmaceutical Sciences 86(6):721-725 (1997).
Li et al., "Solubilization of Flavopiridol by pH Control Combined with Cosolvents, Surfactants, or Complexants", Journal of Pharmaceutical Sciences 88(9):945-947 (1999).
Li et al., "Solubilization of Ionized and Un-ionized Flavopiridol by Ethanol and Polysorbate 20", Journal of Pharmaceutical Sciences 88(5):507-509 (1999).
Li Ming (Ed.). Extracting Technologies and Examples, (pp. 83-85). Chemical Industry Press, Sep. 30, 2006.
Lucky Vitamin, "Derma-E—Hydrating Eye Creme with Hyaluronic Acid and Pycogenol—0.5 oz.," http://www.luckyvitamin.com/PrintProduct.aspx?ProductID=13044.
Mandal et al., "Modulation of the Photophysical Properties of Curcumin in Nonionic Surfactant (Tween-20) Forming Micelles and Niosomes: A Comparative Study of Different Microenvironmentsm," J. Phys. Chem. B 2013, 117, 6957-6968.
MSDS for Genistein from LC Laboratories, downloaded from the internet on May 31, 2012 from the site: http://www.lclabs.com/MSDS/G-6055MSDS.php4.
Patel et al., "Ineraction of Some Pharmaceuticals with Macromolecules I: Effect of Temperature on the Binding of Parabens and Phenols by Polysorbate 80 and Polyethylene Glycol 4000", Journal of Phumaceutunl. Sciences 53(1):94-97 (1964).
Remington, "The Science and Practice Pharmacy", $21^{st}$ Edition, Troy, David B, Editor, Baltimore: Lippincott Williams and Wilkins, p. 324 (2006).
Rodriguez-Tenreiro et al., "Estradiol sustained release from high affinity cyclodextrin hydrogels", European Journal of Pharmaceutics and Biopharmaceutics 66(1):55-62 (2007).
SOOFT | TRIUM collirio; SOOFT italia goup homepage; Trium Eye Drops and Trium Monodose; http://www.00group.it/sooft/en/md_trium_collirio.html.
Taiyouko Co., Ltd, "Taplis," <<http://www.taiyouko.co.jp/export/c_taplis.html>>, retrieved on Mar. 11, 2015.
Tang et al., "Preparation of Self-emulsifying Drug Delivery Systems of Ginkgo biloba Extracts and in vitro Dissolution Studies", Asian Journal of Traditional Medicines 1(3-4):1-4 (2006).
Tommasini et al., "Improvement in solubility and dissolution rate of flavonoids by complexation with β-cyclodextrin", Journal of Pharmaceutical and Biomedical Analysis 35:379-387 (2004).
Tungjai et al., "Spectrophotometric Characterization of Behavior and the Predominant Species of Flavonoids in Physiological Buffer: Determination of Solubility, Lipophilicity and Anticancer Efficacy," The Open Drug Delivery Journal, vol. 2: 10-19 (2008).
Uchegbu et al., "Non-ionic surfactant based vesicles (niosomes) in drug delivery," International Journal of Pharmaceutics 172 (1998) 33-70.
Ultra HA Plus—Hyaluronic Acid Serum from Great American Health, Ultra HA plus—Skin and Joint Hydrating Support, http://greatamericanhealth.com/ultra-ha-plus/.
Wang et al., "Antioxidant effect of natural flavonoids and research developments of its extracting technique", Review 11(5):1-10 (2004).
Yao et al., "Preparation of nobiletin in self-microemulsifying systems and intestinal permeability in rats", J. Pharm. Pharmaceut. Sci. 11(3):22-29 (2008).
Australian Office Action issued in App. No. 2010308571 dated Jan. 15, 2016.
Australian Office Action issued in App. No. 2016202145 dated Nov. 28, 2016.
Canadian Office Action issued in App. No. 2,778,441 dated Jul. 4, 2016.
Chinese Office Action issued in App. No. 201080058485.X dated Nov. 14, 2014 (w/ translation).

(56) References Cited

OTHER PUBLICATIONS

Chinese Office Action issued in App. No. 201080058485.X dated Aug. 11, 2015 (w/translation).
Chinese Office Action issued in App. No. 201180062179.8 dated Jul. 3, 2014 (translation only).
Chinese Office Action issued in App. No. 201180062179.8 dated Mar. 6, 2015 (w/ translation).
European Office Action issued in App. No. 10 774 319.7 dated Nov. 7, 2014.
European Office Action issued in App. No. 10 774 319.7 dated Nov. 10, 2016.
International Search Report issued in PCT/US2010/002821 dated Apr. 18, 2011.
International Search Report issued in PCT/US2011/001802 dated Feb. 8, 2012.
Japanese Office Action issued in App. No. 2012-535193 dated Oct. 14, 2014 (w/ translation).
Japanese Office Action issued in App. No. 2013-534896 dated Aug. 1, 2016 (w/ translation).
Korean Office Action issued in App. No. 10-2013-7013011 dated Sep. 12, 2016 (w/ trans.).
Korean Office Action issued in App. No. 2012-7010346 dated Oct. 7, 2016 (w/ translation).

\* cited by examiner

METHODS OF MAKING AND USING COMPOSITIONS COMPRISING FLAVONOIDS

This patent application is a divisional of U.S. application Ser. No. 13/503,458, filed Apr. 23, 2012, which is a national phase of PCT/US2010/002821, filed Oct. 22, 2010, which claims the benefit of U.S. Provisional Application No. 61/253,857 filed Oct. 22, 2009, the entire contents of each of which are hereby incorporated by reference in this application.

The subject invention relates to novel microparticulate and soluble forms of flavonoids, and their synthesis. The invention also includes novel formulations of such flavonoids and novel methods of manufacturing the flavonoid formulations. The invention also relates to a wide variety of applications of the flavonoid formulations.

BACKGROUND OF THE ART

Flavonoids

The principle plant-derived agents believed to provide protection against cancer are flavonoids and dietary fiber. (Patel, D, et al., *Apigenin and cancer chemoprevention: Progress, potential, and promise, Intl. J. Oncology* 2007 January; 30(1): 233-45.) Chemoprevention is a facet of oncology that focuses on the prevention of cancer through naturally occurring or synthetic agents.

Flavonoids have been shown to act as free radical scavengers, anti-oxidants, superoxide anions, UV absorbers, and lipid peroxy radicals. Flavonoid compounds are also known to be effective in strengthening collagen structures. Further, flavonoids have been shown to exhibit anti-mutagenic, anti-inflammatory, and antiviral effects.

All flavonoids have the same basic chemical structure, a three-ringed molecule. Individual flavonoids in a group differ from each other by the number and position of substituents (the hydroxy, methoxy, or sugar groups).

Flavonoids have the following general formula (Formula I):

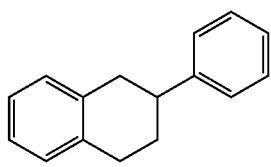

I

Flavonoids comprise approximately 5,000 naturally occurring compounds. A multitude of other substitutions can occur, giving rise to the many types of flavonoids.

Skin Cancer

The development of skin cancer is a major global public health threat. Ultraviolet (UV), e.g., solar ultraviolet B (UVB) and solar ultraviolet (UVA), radiation are the main causes of skin cancer. The incidences of basal cell carcinoma, squamous cell carcinoma, and melanoma continue to rise despite the advent and use of sunscreen agents with high SPF constituents. Early detection and treatment are essential in improving survival rates, yet skin cancer is a cancer that is largely preventable altogether. Current sunscreen formulations have proven inadequate for fully protecting persons from the DNA-damaging effects of UV radiation. Sunscreen usage may sometimes create a false sense of safety as individuals may over expose themselves to sunlight.

Studies have demonstrated that flavones possess anti-oxidant, anti-mutagenic, anti-carcinogenic, anti-inflammatory, anti-proliferative, and anti-progression properties. (Patel, D, et al., *Apigenin and cancer chemoprevention: Progress, potential, and promise, Intl. J. Oncology* 2007 January; 30(1): 233-45.) In addition, Birt and coworkers used an in vivo mouse model to demonstrate that topical application of apigenin prior to UVB-irradiation significantly reduced, by up to 90%, the incidence of skin cancer. (Birt et al., Anti-mutagenesis and anti-promotion by apigenin, robinetin and indole-3-carbinol, Carcinogenesis, June 1986; 7: 959-963) Other groups have demonstrated apigenin's ability to protect mice against colon cancer. (Wang et al, *Cell cycle arrest at G2/M and growth inhibition by apigenin in human cell colon carcinoma cell lines, Molecular Carcinogenesis,* 28: 102-110 (2000))

Researchers have found that apigenin induces reversible, cell-cycle arrests at G1 and G2/M phase of the cell cycle. It was further discovered that apigenin mediates an inhibition on the cell cycle through multiple mechanisms including direct and indirect inhibition of the mitotic kinase p34cdc2, as well as the induction of the cell cycle inhibitor p21WAF1 in a p53-dependent manner. (Lepley D M, et al., *The chemopreventative flavonoid apigenin induces G2/M arrest in keratinocytes, Carcinogenesis,* 17, 2367-75 (1996))

Loss of G1/S and/or G2/M cell cycle checkpoint controls leads to transformation and cancer progression. Initiation and progression through the cell cycle is largely controlled by proto-oncogenes that promote cell proliferation and tumor suppressor genes that function to slow or halt cell growth. Mutations in either proto-oncogenes and/or tumor suppressor genes predispose cells to a compromised G1/S checkpoint by shortening the length of time spent in G1 or G2/M.

Other Skin Disorders

Kang, Ecklund, Liu & Datta, (*Arthritis Research & Therapy* 2009, Vol. 11) taught that increasing the bioavailability of dietary plant-derived COX-2 and NF-κB inhibitors, such as apigenin, could be valuable for suppressing inflammation in lupus and other Th17-mediated diseases like psoriasis. Apigenin, a non-mutagenic dietary flavonoid, suppresses lupus by inhibiting autoantigen presentation for expansion of autoreactive Th1 and Th17 cells.

Dimethyl sulfoxide (DMSO) has been widely used in vivo studies as a solvent for many water insoluble flavonoids including apigenin. However, due to toxicity concerns, dimethyl sulfoxide is not recommended as a solvent when a topical formulation is considered for human applications. Nearly all apigenin studies devoted to anti-skin cancer topical treatments have utilized dimethyl sulfoxide (DMSO) as the solvent of choice due to apigenin's poor solubility in water (<0.005 milligram per milliliter (mg/ml)) and other aqueous solvents. (Li et al, *Evaluation of Apigenin and [G-$^3$H], Apigenin and analytical method development, J. of Pharmaceutical Sciences.* Vol. 86, No. 6, June 1997).

Furthermore, many flavonoids are practically insoluble in water and almost all solvents suitable for pharmaceutical, cosmetic, and food additive formulations, preventing their direct use as components in topical compositions. Thus, there is a need for methods for enhancing the bioavailability of these flavonoids including flavones by utilizing acceptable ingredients for topical, pharmaceutical, peritoneal, nutraceutical and medical food applications.

Other Disease

As is typical for phenolic compounds, flavonoids act as potent antioxidants and metal chelators. They also have long been recognized to possess antiinflammatory, antiallergic, hepatoprotective, antithrombotic, antiviral, and anticarcinogenic activities.

The flavones and catechins are very powerful flavonoids for protecting the body against reactive oxygen species (ROS). Body cells and tissues are continuously threatened by the damage caused by free radicals and ROS which are produced during normal oxygen metabolism or are induced by exogeneous damage. The anti-inflammatory activity of flavonoids in many animal models has been reported Flavones/flavonols such as apigenin, luteolin, kaempferol, quercetin, myricetin, fisetin were reported to possess Lipoxygenase (LO) and Cyclo-oxygenase (COX) inhibitory activities. Jachak S M *Natural products: Potential source of COX inhibitors. CRIPS* 2001; 2(1):12-15.

Methods of Forming Nanoparticles

US Patent Application US 2010 0047297 to Petersen discloses nanocrystals of compounds such as apigenin for use in topical cosmetic formulations.

U.S. Pat. No. 5,145,684 to Liversidge et al discloses methods to form nanocrystals of drugs by mechanical means producing shear, impact, cavitation and attrition forces.

U.S. Pat. No. 5,510,118 to Bosch et al similarly discloses methods to form nanocrystals of drugs by mechanical means producing shear, impact, cavitation and attrition forces.

U.S. Pat. No. 5,510,118 to Muller et al discloses high pressure homogenization methods for the formation of nano particulate suspensions.

U.S. Pat. No. 4,826,689 describes a process for the preparation of amorphous particles of a solid by infusing an aqueous precipitating liquid into a solution of the solid in an organic liquid under controlled conditions of temperature and infusion rate, thereby controlling the particle size.

Aqueous suspensions of a solid material can be prepared by mechanical fragmentation, for example by milling. U.S. Pat. No. 5,145,684 describes wet milling of a suspension of a sparingly soluble compound in an aqueous medium.

Crystalline dispersions obtained directly by precipitation are known in the art to be influenced by agitation of the solutions. Various methods of agitation are known in the art, for example mechanical mixing, vibration, microwave treatment and sonication (see e.g. WO 01/92293). Agitation is achieved using a number of techniques including ultrasonic agitation. The resulting crystals generally have a mass median diameter of 1 to 6 microns.

U.S. Pat. No. 5,314,506 describes a crystallization process in which a jet of a solution containing a substance is impinged with a second jet containing an anti-solvent for the substance. The rapid mixing produced by the impinging jets results in a reduction of the crystals so formed compared to conventional slow crystallization processes. The smallest crystals disclosed are about 3 microns and the majorities are in the range of from 3 to 20 microns.

EP 275 607 describes a process wherein ultrasound energy is applied to a suspension of crystals in a liquid phase, the ultrasound being used to fragment the pre-formed crystals. Generally, the volume mean diameter of the resulting crystals was 10 to 40 microns.

WO 03/059319 describes the formation of small particles by adding a solution of a drug dissolved in a water immiscible organic solvent to a template oil-in-water emulsion after which the water immiscible organic solvent is evaporated off. Water is then removed, e.g. using a spray-drying process to obtain a powder.

U.S. Pat. No. 6,197,349 describes a process for the formation of amorphous particles by melting a crystalline compound and mixing the compound with a stabilizing agent, e.g. a phospholipid, and dispersing this mixture in water at elevated temperature using high pressure homogenization, after which the temperature is lowered.

PCT/US2006/020905 to Doseff discloses methods of treating inflammation with apigenin or its derivatives.

US Patent application US 2008/0227829 to Hammerstone discloses methods of treating subjects with a neurogenic compound including apigenin.

U.S. Patent application US 2007/0154540 to Park et al discloses the use of apigenin as a chondroregenerative agent for the treatment of osteoarthritis.

U.S. Patent application US 2007/0189680 to Bing-Hua et al discloses the use of apigenin for chemoprevention and chemotherapy combined with therapeutic reagents.

U.S. Patent application US 2006/0067905 to Lintnera et al discloses the use of apigenin as a vasodilatory agent for treating baldness.

Hyaluronic Acid (HA)

Hyaluronic acid is an anionic, nonsulfated glcosaminoglycan distributed widely throughout connective, epithelial, and neural tissues. It is unique among glycosaminoglycans in that it is nonsulfated, forms in the plasma membrane instead of the Golgi, and can be very large, with its molecular weight often reaching the millions. One of the chief components of the extracellular matrix, hyaluronic acid contributes significantly to cell proliferation and migration.

Polysaccharides such as HA are relatively complex carbohydrates. Polysaccharides are polymers made up of many monosaccharides joined together by glycosidic bonds. The glycosidic bonds are therefore large, often branched, macromolecules. Polysaccharides have been useful in cosmetic and medical applications. For example, HA finds use as a structure stabilizing filler for dermal applications.

U.S. Patent application 2005/0271692 to Gervasio-Nugent et al discloses topical cosmetic compositions which include flavonoids and hyaluronic acid.

U.S. Patent application 2006/021625 to Morariu discloses topical formulation and methods of use for improving the appearance of aged skin. Preferred components include flavonoids such as apigenin and hyaluronic acid.

Surfactants

Polysorbates (commercially also known as Tweens) are nonionic surfactants and emulsifiers derived from polyethoxylated sorbitan and fatty acids. They are often used in foods and in cosmetics to solubilize essential oils into water-based products. The Polysorbates are viscous, water-soluble pale yellow liquids. Polysorbates also help to form emulsions by reducing the surface tension of the substances to be emulsified. Polysorbates have been recognized for their ability to help ingredients to dissolve in a solvent in which they would not normally dissolve. Polysorbates function to disperse oil in water as opposed to water in oil.

Polysorbates are produced by reacting the polyol, sorbitol, with ethylene oxide. The polyoxyethylenated sorbitan is then reacted with fatty acids obtained from vegetable fats and oils such as stearic acid, lauric acid, and oleic acid. Surfactants that are esters of plain (non-PEG-ylated) sorbitan with fatty acids are usually referred to by the name Span.

U.S. Pat. No. 7,329,797 to Gupta discloses antiaging cosmetic delivery systems which includes the use of flavonoids including apigenin as an anti inflammatory agent and polysorbate surfactants as emulsifying agents, U.S. Patent Application 2006/0229262 to Higuchiet al disclose pharmaceutical compositions for the treatment of infections for treatment of infections with a drug resistant bacterium including flavonoids such as apigenin as an active ingredient and polysorbates as emulsifying agents.

Research studies have provided evidence that apigenin plays a critical role in the amelioration of the pathogenetic process of asthma. Recent epidemiological studies reported that a low incidence of asthma was significantly observed in a population with a high intake of flavonoids.

In view of the foregoing, it is most desirable to incorporate flavonoids, such as the flavones apigenin and luteolin, as part of topical formulations to aid in the prevention and/or treatment of skin damage or skin cancer resulting from the effects of sun exposure and also to provide a skin treatment composition useful in the treatment of a variety of dermatological conditions.

SUMMARY OF THE INVENTION

The subject invention relates to a composition comprising a hydrated microparticulate flavonoid, and a carrier. Typically, the solubility in water of the flavonoid is less than 1 mg/ml, or less than 0.1 mg/ml. The microparticulate flavonoid has an average size of 200-500 nanometers, or advantageously has an average size of 250 nanometers. In a preferred embodiment, the composition is a pharmaceutical composition and said carrier is a pharmaceutically acceptable carrier. The composition can include hyaluronic acid, and the carrier typically includes a compound that prevents or reduces agglomeration of the microparticles, a dispersant or penetration enhancer. In one embodiment the composition is in the form of a colloid, nanosupension or emulsion. The composition can be a nutraceutical, dietary supplement, food supplement, or medical food.

Another embodiment of the invention relates to a composition comprising a flavonoid, and a heat stable flavonoid solubilizing compound such as a surfactant, wherein said composition is formed by mixing the flavonoid and the compound to a temperature where said flavonoid is dissolved in said compound. Typically, the composition further includes an alcohol selected from the group consisting of ethanol, isopropyl and benzyl alcohol, ethoxydiglycol and dimethyl isosorbide. In a preferred embodiment, the composition is a pharmaceutical composition and said carrier is a pharmaceutically acceptable carrier. The composition can include hyaluronic acid, and or a penetration enhancer. In one embodiment the composition is in the form of an emulsion or microemulsion. The composition can be a nutraceutical, dietary supplement, food supplement, or medical food.

Another embodiment of the invention is a patch for application of a flavonoid transdermally comprising a substrate having two sides, a first side having a composition of the invention and an adhesive, and a second side with a material which is impermeable to the composition and adhesive on the first side.

Another embodiment of the invention is a method of producing a hydrated flavonoid, comprising mixing a flavonoid with an alkali metal hydroxide to form an aqueous solution of an alkali metal flavonoid salt; acidifying the aqueous solution of an alkaline metal flavonoid salt with an acidic agent to a pH level of less than 7 to form a hydrated flavonoid precipitate, wherein the acidifying step is typically done under conditions producing nanofibers having an average size of 50-1000 nanometers, more advantageously 200-500 nanometers, with an aspect ratio measuring greater than 20. After the acidifying step can be the step of adjusting the pH to less than 7, and filtering the precipitate. The precipitate can then be washed and dried.

Another embodiment of the invention is a method of producing a hydrated flavonoid, comprising dissolving a flavonoid in a non-toxic organic solvent to form a mixture; and adding water to the mixture to form a hydrated flavonoid precipitate; wherein the adding water step is done under conditions producing nanofibers having an average size of 50-1000 nanometers, more advantageously 200-500 nanometers, with an aspect ratio measuring greater than 20. Typically, the dissolving step is done at a temperature of about 20° C. to below the boiling point of the organic solvent. The organic solvent can be selected from the group consisting of dimethyl isosorbide, ethoxydiglycol, and dimethylsulfoxide.

Another embodiment of the invention is a method of forming a topical formulation of a hydrated flavonoid comprising mixing a flavonoid with an alkali metal hydroxide in water to form an alkali metal flavonoid salt solution; adding the alkali metal flavonoid salt solution to a dermatologically acceptable carrier, and adjusting the pH of the formulation to a dermatologically acceptable pH (e. g. 4-8), wherein the adjusting the pH step is done under conditions producing flavonoid nanofibers having an average size of 50-1000 nanometers.

Another embodiment of the invention is a method of preparing a topical formulation of a hydrated flavonoid comprising: solubilizing a flavonoid in an alcohol; adding the alcohol solubilized flavonoid to a dermatologically acceptable carrier, adjusting the pH of the formulation to a dermatologically acceptable pH (e.g. 4-8) wherein the adjusting the pH step is done under conditions producing flavonoid nanofibers having an average size of 50-1000 nanometers.

A method of preparing a topical formulation of a flavonoid comprising: adding a flavonoid to an emulsion carrier to form a mixture; heating (e.g. to about 120° F.-170° F.) the mixture until it has the approximate viscosity of water (or a viscosity where a dispersion can be done), forming a dispersion of microparticles in the mixture. Typically, the emulsion is an oil in water, or water in oil emulsion and the emulsion includes a stabilizer, a dispersant or a surfactant, or another stabilizing agent to inhibit microparticle agglomeration. In one embodiment, the forming a dispersion step is accomplished using sonication or high pressure homogenization.

Another embodiment of the invention is a method of preparing a solubilized flavonoid composition comprising: mixing flavonoid particles with a heat stable flavonoid solubilizing compound such as a surfactant, to form a mixture, heating the mixture to a temperature where the flavonoid particles are solubilized, and cooling the solution. In an advantageous embodiment, the heat stable flavonoid solubilizing compound is a nonionic surfactant. Typically, the mixture is stirred while heating, and up to 10 wt % of a flavonoid compound is added. In an advantageous embodiment, the surfactant is a polysorbate. After the heating or cooling step is the step of adding the solution to a dermatological, oral, injectable, dermal patch, or aerosol carrier. Typically, a small chain alcohol selected from the group consisting of ethyl alcohol, isopropyl alcohol, benzyl alcohol, ethoxydiglycol and dimethyl isosorbide, is added to the solution to form a solution with a reduced viscosity.

The invention also relates to a method of reducing and/or preventing the effects of sun exposure comprising applying a therapeutically effective amount of a sunscreen formulation to the skin comprising a hydrated or solubilized flavonoid, and a carrier that permits delivery of the flavonoid to the stratus corneum and the epidermis. In another embodiment, the formulation additionally comprises mineral oxides to provide additional ultraviolet sun exposure protection.

In another embodiment, the invention relates to a method of treating the effects of sun exposure comprising applying a therapeutically effective amount of a formulation to sun damaged skin comprising a hydrated or solubilized flavonoid, and a carrier that permits delivery of the flavonoid to the stratus corneum and the epidermis.

In another embodiment, the invention relates to a method of reducing the likelihood of or treating cancer in a mammal comprising administering to a mammal in need of such treatment a prophylactic amount or a therapeutically effective amount of a formulation of the invention.

In another embodiment, the invention relates to a method of treating inflammation in a mammal comprising administering to a mammal in need of such treatment a therapeutically effective amount of a formulation of the invention.

In another embodiment, the invention relates to a method of treating a skin disease or disorder such as acne, alopecia, dermal sensitization and irritation, dry skin (xerosis, ichthyosis), fungal infections, and rosacea, contact dermatosis, in a mammal comprising administering to a mammal in need of such treatment a therapeutically effective amount of a formulations of the invention.

In another embodiment, the invention relates to a method of treating autoimmune disease such as psoriasis, lupus, arthritis in a mammal comprising administering to a mammal in need of such treatment a therapeutically effective amount of a formulation of the invention.

In another embodiment, the invention relates to a method of treating allergic disease allergies, asthma, atopic dermatitis/eczema comprising administering to a mammal in need of such treatment a therapeutically effective amount of a formulation of the invention.

In another embodiment, the invention relates to a method of treating or reducing the likelihood of a TNFα related disease in a mammal comprising administering to a mammal in need of such treatment a therapeutically effective amount or aprophylactic amount of a flavonoid formulation of the invention.

In another embodiment, the invention relates to a method of treating or reducing the likelihood of an IL-1β related disease in a mammal comprising administering to a mammal in need of such treatment a therapeutically effective amount or a prophylactic amount of a flavonoid formulation of the invention.

Another embodiment of the invention is a method for the formation of a vitamin flavone homogeneous solid mixture comprising: heating a vitamin until molten, wherein the vitamin is selected from the group consisting of Vitamin B3, Vitamin B5, and combinations comprising at least one of the foregoing vitamins; dissolving a flavone in the molten vitamin to form the vitamin flavone liquid mixture; and cooling the vitamin flavone liquid mixture to form a homogenous solid mixture.

DETAILED DESCRIPTION OF THE INVENTION

Figure 1:
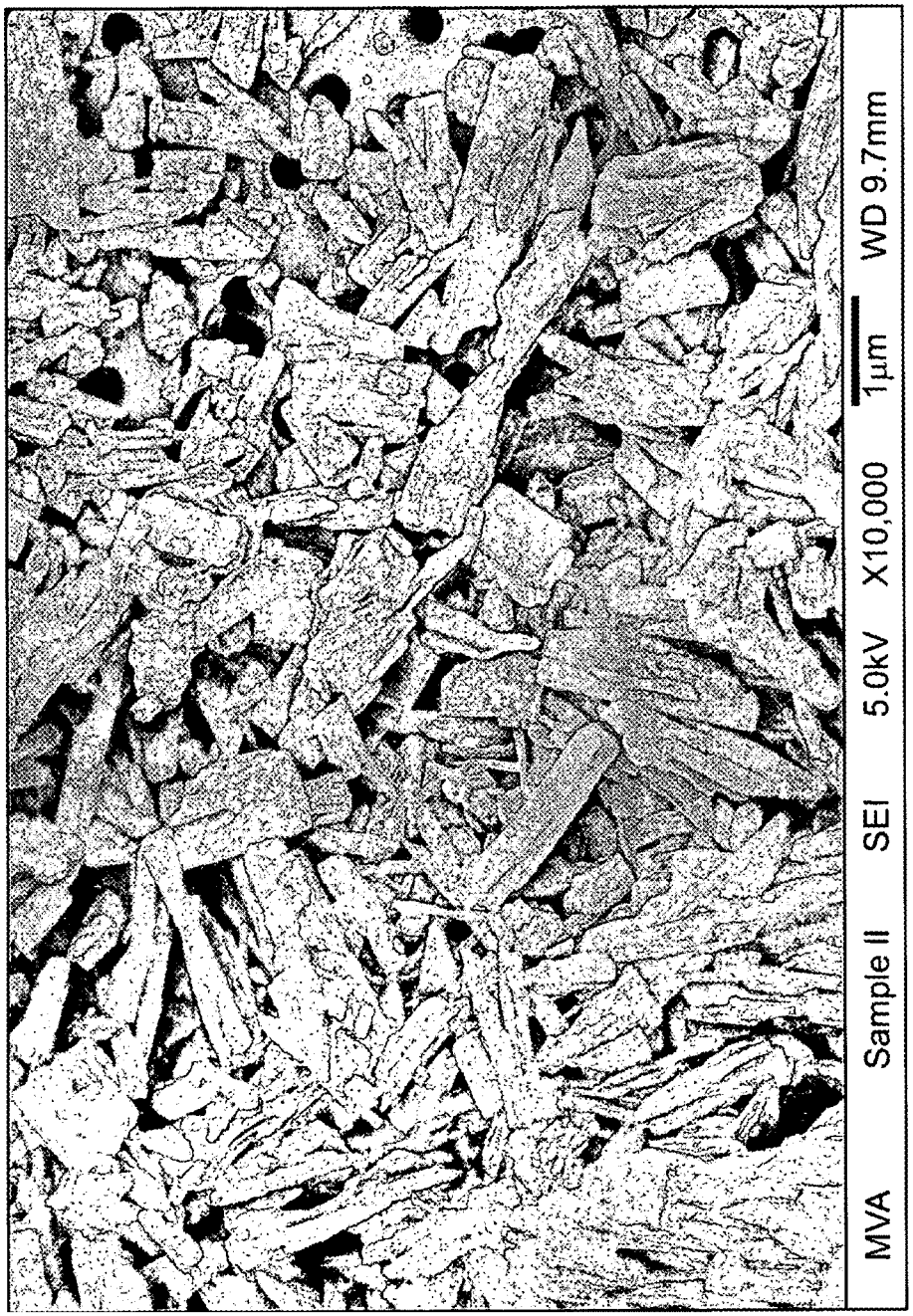
FIG. 1 is a typical Scanning Electron Microscopy (SEM) photo detailing the crystal shape of the unprocessed apigenin powder at a magnification of 10,000×.

The subject invention relates to new forms of flavonoids, formulations, food supplements, and pharmaceutical compositions, as well as methods for making and using the same.

I—Compounds of the Invention

The chemical structures of some commonly occurring plant flavonoids are listed in Table I.

TABLE I

CHEMICAL STRUCTURES OF SOME COMMONLY OCCURING PLANT FLAVONOIDS

| Structure | Representative flavonoids |
|---|---|
| [Flavones structure with $R_1$, $R_2$, $R_3$ substituents] | $R_1$ = H, $R_2$ = OH; Apigenin $R_1$ = $R_2$ = OH: Luteolin |

Flavones

TABLE I-continued

CHEMICAL STRUCTURES OF SOME COMMONLY OCCURING PLANT FLAVONOIDS

| Structure | Representative flavonoids |
|---|---|
| Flavonols | R2 = OH, R1 = R3 = H: Kaempferol<br>R1 = R2 = OH, R3 = H: Quercetin<br>R1 = R2 = R3 = OH: Myricetin |
| Isoflavones | R1 = H: Daidzein<br>R1 = OH: Genistein |
| Flavanols | R1 = R2 = OH, R3 = H: Catechins<br>R1 = R2 = R3 = OH: Gallocatechin |
| Flavanones | R1 = H, R2 = OH: Naringenin<br>R1 = R2 = OH: Eriodictyol<br>R1 = OH, R2 = OCH3: Hesperetin |
| Anthocyanins | R1 = R2 = H: Pelargonidin<br>R1 = OH, R2 = H: Cyanidin<br>R1 = R2 = OH: Delphinidin<br>R1 = OCH3, R2 = OH: Petunidin<br>R1 = R2 = OCH3: Malvidin |

Flavonoids include the flavones (e.g., apigenin, luteolin), flavonols (e.g., quercetin, myricetin), flavonones (e.g., narigenin, hesperidin), flavonols (or catechins) (e.g., epicatechin, gallocatechin), anthocyanidins (e.g., cyaniding, pelargonidin), and isoflavones (e.g., genistein, daidezin).

Apigenin is a member of the flavone structural class and is chemically known as 4',5,7,-trihydroxyflavone. Apigenin has the following structural formula (Formula II):

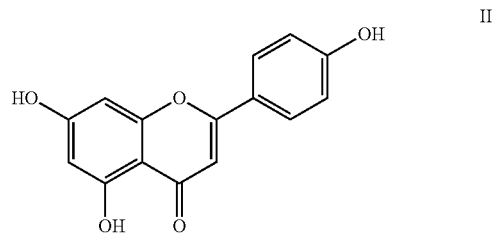 [SMILES: O=c1cc(-c2ccc(O)cc2)oc2cc(O)cc(O)c12]

Luteolin is also a member of the flavone structural class and is chemically known as 3',4',5,7-tetrahydroxyflavone. Luteolin has the following structural formula (Formula III):

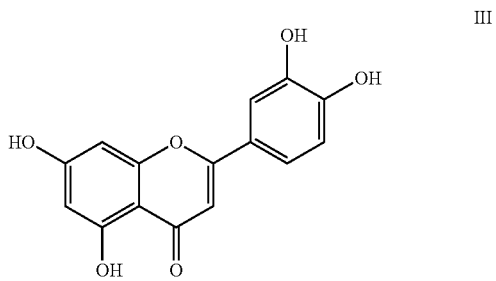 [SMILES: O=c1cc(-c2ccc(O)c(O)c2)oc2cc(O)cc(O)c12]

Both apigenin and luteolin are practically insoluble (i.e., a solubility of less than 1 mg/ml) in water and nearly all solvents suitable for pharmaceutical, cosmetic, and food additive formulations.

The term "hydrated flavonoid" as used herein relates to a precipitate of a flavonoid formed by the addition of an acid to the alkali metal (e.g. Na+ or K+) salt form of the flavonoid, or formed by the addition of water to the flavonoid solubilized in a non toxic (e.g. not DMSO) organic solvent. Advantageously, the precipitate is formed under conditions producing nanofibers having an average size of 50-1000 nanometers, more advantageously 200-500 nanometers, with an aspect ratio measuring greater than 20.

Likewise, the term "hydrated flavone" (e.g. "hydrated apigenin") as used herein relates to a precipitate of a flavone (e.g. apigenin) formed by the addition of an acid to the salt form of the flavone, (e.g. salt of apigenin), or formed by the addition of water to the flavone solubilized in a non toxic (e.g. not DMSO) organic solvent. Advantageously, the precipitate is formed under conditions producing nanofibers having an average size of 50-1000 nanometers, more advantageously 200-500 nanometers, with an aspect ratio measuring greater than 20.

The teachings of this invention are applicable to poorly soluble flavonoids having a solubility in water less than 1 mg/ml, and particularly less than 0.1 mg/ml.

In one embodiment, the hydrated flavonoid is in an isolated state, i.e. in a substantially purified form, i.e. greater than 95% pure, advantageously greater than 98% pure, and most advantageously greater than 99% pure.

II—Methods of Making the Hydrated Flavonoid Microparticles

Methods are disclosed herein for producing hydrated flavonoids of relatively water insoluble flavonoids, such as apigenin and/or luteolin. For example, the hydrated flavones can comprise hydrated apigenin, hydrated luteolin, or a combination thereof, or one of the forgoing hydrated flavones and another flavone or bioflavone. The preparation of these hydrated flavonoids has resulted in the enhanced bioavailability of the flavonoids allowing for the addition of flavonoids to a variety of acceptable pharmaceutical and cosmetic carriers, e.g. aqueous alcoholic solvents.

In one embodiment, a hydrated flavonoid or flavone is formed by: the mixing of a flavonoid with an alkali metal component (e.g., alkali metal hydroxide(s) and/or alkaline metal salt(s)) to form an alkali metal flavonoid salt; adjusting (e.g., acidifying) the alkali metal flavonoid salt with an agent (e.g., an acidic agent) to a pH level of less than or equal to 7.5 resulting in a gel like precipitate of the flavonoid; filtering out the hydrated flavonoid; and washing of the hydrated flavonoid (e.g., with water such as distilled water) to remove alkaline salts and excess acidifying agent; and, optionally, drying of the hydrated flavonoid.

To form fine submicron particles, control of the acidification process is required. This includes the rapid addition and mixing of the acidifying agents with the alkaline flavonoid salt solutions until the microparticulates are uniformly distributed. The mixing of the acidifying agent, at temperatures advantageously from 1 to 10° C., with the alkaline salt solution is done such that the ratio of mixing time to precipitation time is minimized (advantageously, a ratio of 1-5, and most advantageously, a ratio of 1-2). These ratios contribute to increasing the rate of nuclei formation and limits the rate of crystal growth. Typically, the microparticulate hydrated flavonoid has an average size of 50-1000, advantageously 200-500 nanometers, e.g. averaging 250 nm.

Exemplary flavones include, for example apigenin, luteolin, or a combination thereof. Thus, the method can prepare hydrated flavones including hydrated apigenin, hydrated luteolin, or a combination thereof.

Exemplary alkaline metal hydroxides include sodium hydroxide (NaOH), potassium hydroxide (KOH), lithium hydroxide (LiOH), as well as combinations comprising at least one of the foregoing hydroxides.

Exemplary alkali metal salts include citrates (e.g., sodium citrate, potassium citrate, lithium citrate), and carbonates (e.g., sodium carbonate, potassium carbonate, lithium carbonate), as well as combinations comprising at least one of the foregoing salts.

The hydrated flavonoids and hydrated flavones are exceptionally beneficial as additives to topical, oral, and injectable formulations for their anti-cancer, anti-oxidant, anti-inflammatory, UV skin protection and other desirable activities.

Filtration

Unexpectedly, it was found that filtration process to separate the hydrated flavonoid precipitate from solution was carried out with relative ease without the addition of surfactants/dispersants when the pH of the solution is acidified to a pH<7, advantageously <6. Under these conditions, there is entrapment of nearly all nanoparticles (or nanofibers) on a 2 micron filter such that relatively insignificant quantity of nanofibers appeared in the filtrate. If the precipitation process is carried out at a slightly alkaline pH and in the presence of a surfactant/dispersant, difficulty is experienced in separating the hydrated flavonoid from the liquid solution.

Filtration of nanoparticulates has been previously used to purify nanoparticulate dispersions; however, filtrate removal rates were limit to <0.05 ml/min*cm$^2$ and the dispersion could only be concentrated by a factor of ~1/5. Longer filtration times enable particle growth via Ostwald ripening and coagulation. Filtration rates >1 ml/min*cm$^2$ were achieved from the dispersion solution with a concentrated factor of 1/15 of the gel-like hydrated flavonoid precipitates.

The complete removal of the dispersion medium from nanoparticulates generally requires separation processes such as centrifuging, lyophilization (freeze-drying), and/or flash spray drying processing. For several applications/formulations of the subject invention, the hydrated flavones/flavonoids precipitates are directly added to cosmetic and nutraceutical formulations without further processing to completely remove the residual water content.

The subject invention addresses the need for the effective removal of the dispersion medium without resorting to additional evaporative or other processing for further water removal for applications where complete water removal is not required. Prior to the subject invention, the recovery of the nanoparticles from solution and further processing of the nanocrystals in the solid state was a formidable challenge. The subject invention provides novel and rapid techniques for particle recovery and solvent removal for subsequent processing. The common techniques for solvent and dispersion media removal which include spray drying, freeze drying and ultrafiltration, are thus not required.

Production of Nanoparticles Via Mechanical Processes

High Pressure Homogenization

High pressure homogenization (HPH) is a mechanical process to prepare submicron size particulates in a suspension containing poorly water soluble particulates. The principle of forming nanosuspensions is based on the cavitation forces created within the high pressure homogenizer. The particle size reduction achieved is based on several factors which include the properties of the particulates, the processing pressure and number of cycles applied.

In one embodiment of the subject invention: (1) the flavonoid particles less than 20 microns are dispersed in a stabilizer solution to form a suspension, and (2) the suspension is then homogenized at a high pressure for several cycles until the nanosuspension with the desired size is prepared. During homogenization, particles are fractured by cavitation, high-shear forces and the collision of the particles against each other. In the homogenization gap, the dynamic pressure of the fluid increases with the simultaneous decrease in static pressure below the liquid boiling point at room temperature. Consequently the liquid starts to boil and forms gas bubbles at room temperature, and the bubbles will implode when the suspension leaves the gap and normal air pressure is reached. The implosion forces are sufficiently high to break down the microparticles into nanoparticles. See Example 18 below.

Sonication

Dispersion and deagglomeration by sonication are a result of ultrasonic cavitation. When exposing liquids to ultrasound, the sound waves that propagate into the liquid result in alternating high-pressure and low-pressure cycles. This applies mechanical stress on the attracting forces between the individual particles. Ultrasonic cavitation in liquids causes high-speed liquid jets of up to 1000 km/hr (approx. 600 mph). Such jets press liquid at high pressure between the particles and separate them from each other. Smaller particles are accelerated with the liquid jets and collide at high speeds. This makes ultrasound an effective means for the dispersing but also for the milling of micron-size and sub micron-size particles. See Example 17 below Such a simple sonication processing treatment is of value for both the nutraceutical and pharmaceutical applications of flavonoids.

Other methods for producing nanoparticulates include microprecipitation processes as described in U.S. Pat. Nos. 4,826,689 and 5,314,506; solvent/anti-solvent methods as described in WO 01/92293, 96/32095, 00/44468, 00/38811; and melt emulsification processes as described in WO98/32095 & 99/59709.

III—Methods of Preparing the Flavonoid Formulations

A. Methods of Preparing the Microparticulate Flavonoid Formulations

In one embodiment of the invention, a flavonoid such as apigenin is loaded into a carrier in its salt form, which is dissolvable in aqueous phase, the pH is then lowered while agitating the formulation. When the system pH is lowered, the flavonoid (e.g., apigenin) begins to precipitate out as finely dispersed micro-particulates. Th pH is adjusted to a dermatologically acceptable level, i.e. non-toxic and non irritating to the skin. The continuous agitation prevents the flavonoid from forming large crystals and prevents its agglomeration. The final system contains both soluble and dispersed micro-particulate flavonoid (e.g. apigenin) in the formulation.

The suspended micro-particulate form is capable of penetrating the skin layers and is available as a reservoir to replenish dissolved flavonoid, e.g. apigenin, that has been expended so as to maintain a sustained flavonoid rate of bioavailability.

Another embodiment of the invention is a method for preparing a composition comprising solubilizing a flavonoid in a non-toxic organic solvent (not DMSO) such as an alcohol; adding the product to a carrier, e.g., a dermatologically acceptable carrier, to form a flavonoid containing formulation; optionally adjusting the pH of the formulation to a pH of 4 to 8; and mixing the composition to disperse (e.g., uniformly disperse to prevent potential agglomerates from forming) the flavonoid.

The formulations can be prepared in various methods, such as:

1) the formation of flavonoid can be dissolved in aqueous based solvents (such as ethoxydiglycol and/or dimethyl isosorbide) and added as a constituent of a topical vehicle;

2) alkali metal flavonoid salt can be added as a constituent of a vehicle followed by acidification to dermatologically acceptable pHs—typically near neutral pHs, resulting in solubilized flavonoid together with dispersed micro-particulate flavonoid.

Another embodiment is the combination of methods 1 and 2.

The components of the formulation can be combined by sequential addition, with or without preference to order, followed by mixing to form a mixture. For example, components that are water soluble will generally be combined to form an aqueous phase, and components that are not miscible in the aqueous phase will generally be combined to form an oil phase. Thereafter, the two phases can be emulsified and then combined. Alternatively, compositions can be prepared by admixing, such as in a one-pot system.

The method of producing a composition can comprise dissolving flavonoid(s) in a solvent(s) to form a solution, and adding the solution to a vehicle to form the formulation. The solution can be added to the vehicle while vigorously stirring, e.g., so as to uniformly disperse the dissolved hydrated flavonoid(s) within the vehicle.

If the solubility limits of the flavonoid such as apigenin are exceeded within a given formulation with the addition of the dissolved flavonoid within a solvent or solvent mixture, then dispersed micro-particulates are formed. A dispersant, surfactant, and/or polymer thickener in the carrier can reduce micro-particulate agglomeration.

In general, the ratio of the suspended and dispersed micro-particulate form of the flavonoid such as apigenin, to the dissolved form within the vehicle is increased as the pH level of the formulation is reduced from the slightly basic (pH of approximately 8 (e.g., pH of 7 to 9)) to the moderately acidic (pH of approximately 4 (e.g., a pH of 3.5 to 5)).

Formulations can be prepared by solubilizing flavonoid(s) in an alcohol to form a concentrated alcohol solubilized solution; adding the concentrated alcohol solubilized solution to a vehicle before adjusting the pH to a pH of 5 to 8. Desirably, as the alcohol solubilized solution is added, the vehicle is sufficiently mixed to uniformly disperse the flavonoid(s). Optionally, the method can further comprise adding an additive to the solubilized solution and/or to the vehicle.

In-Situ Methods at Reduced Viscosity of the Emulsified Carrier

Previous practices required that submicron particulates first be formed via a variety of processing methods which include mechanical (pearl milling, high pressure homogenization (HPH)), precipitation etc. Further, time-consuming and costly filtration, evaporative techniques (flash spray drying, freeze drying etc) are required to separate the liquid medium from the submicron size particulates prior to inclusion within topical formulation.

In another embodiment of the invention, unprocessed apigenin powder or another relatively insoluble flavonoid, is directly added to an oil in water, or water in oil emulsion, and processed via sonication and/or HPH techniques to achieve a dispersion of microparticulates. A requirement of the method is that sonication and/or HPH processing of the emulsions be carried out at elevated temperatures such that the viscosity of the fluid mixture is reduced to approximately viscosity levels of water. Fine submicron particulates are formed when the fluid mixtures are sonicated at temperatures of about 120° F.-170° F. Further, the stabilizing additives of the emulsion such as dispersants, surfactants and other stabilizing agents serve to inhibit further potential particulate agglomeration. This in-situ processing methodology eliminates costly and time consuming processing steps to achieve submicron sized particulates within formulations, including topical formulations. See Example 20.

B. Methods of Preparing the Solubilized Flavonoid Formulations

The subject invention relates to methods for substantially increasing the solubility concentrations of relatively water insoluble flavonoids with a heat stable non-toxic flavonoid solubilizing compound such as nonionic surfactant compounds, including polysorbates, comprising the steps of:

a) mixing a flavonoid compound in a heat stable flavonoid solubilizing compound to form a mixture, b) heating the mixture while stirring to a temperatures where the flavonoid compound particulates are solubilized and the resulting mixture forms a clear solution, and c) cooling the solubilized flavonoid solution.

In other embodiments, after step b) or c) is the step of adding the solubilized flavonoid mixture to a dermatological, oral, injectable, dermal patch, or aerosol carrier.

In another embodiment is the step of adding an alcohol such as ethyl alcohol to the solubilized flavonoid mixture to form a soluble flavonoid solution with a reduced viscosity.

Other advantageous solvents to reduce the viscosity level the solubilized flavonoid mixture include small-chain alcohols such as isopropyl and benzyl alcohol and ethoxydiglcohol and dimethyl isosorbide.

As used herein, "a heat stable flavonoid solubilizing compound" is a compound that is stable up to at least 200° C., and which upon thermal treatment (heating) when mixed with a flavonoid, solubilizes the flavonoid, and upon cooling to ambient temperatures, continues to solubilize the flavonoid. Advantageously, the flavonoid solubilizing compound is capable of continuing to solubilize the flavonoid at ambient temperatures for extended periods of time.

Besides polysorbates, other heat stable (i.e. stable up to 200° C. or higher) solubilizing compounds that allow for enhanced solubility concentration levels of flavonoids employing the high temperature methods of this disclose include: hyper branched or dendrimeric polyethylene oxide polymer (including sorbitan polyethylene oxide dendrimer), hyperbranched polyethylene glycol, hyperbranched polypropylene glycol, ethoxylated aliphatic alcohols, polyoxyethylene surfactants, carboxylic esters, polyethylene glycol esters, anhydrosorbitol ester and its ethoxylated derivatives, glycol esters of fatty acids, and fatty amine ethoxylates.

Apigenin/Polysorbate 80 formulations can be made as follows:
Apigenin powder & viscous liquid Polysorbate 80 are mixed in the ratio from about 5 to 10 wt % of apigenin to 95 to 90 wt % Polysorbate 80. A small quantity (5-10 wt %) of D.I. water and optionally acetone and/or ethyl alcohol is optionally added to facilitate the blending of the mixture.
This mixture is thoroughly stirred to form a thick paste-like blend.
The mixture is then slowly heated to relatively high temperatures (about 100 to 150° C.) while stirring. The heating is accompanied by the boiling off of the water and also volatile constituents present in the Polysorbate 80.
Upon the removal of the volatiles and heating to temperatures in excess of about 200 to 300° C., a dark brown transparent liquid results such that all the solid apigenin is solubilized in the Polysorbate 80 mixture.
Upon cooling to ambient temperatures, a thick viscous brown liquid results. The higher the apigenin content— the darker the resulting color.
Based on a 4.05% concentration of apigenin in the viscous apigenin polysorbate 80 liquid, the content of apigenin is 40.5 mg/ml or 40, 500 ppm.

It was unanticipated that high temperature levels were necessary to cause the high solubility level of apigenin and other relatively water insoluble flavonoids.

The use of apigenin/polysorbate 80 in an alcohol solution can deliver apigenin and other relatively insoluble flavonoids to the desired target location. The invention includes methods of combining heat stable compounds with the proper balance of polarity characteristics such as surfactants, with other flavonoids to achieve elevated concentration levels of the other flavonoids. Examples 14 and 15 show formulations of other flavonoids and polysorbates.

In Example 21, the formulations of the subject invention delivered significant apigenin concentrations to both the epidermal and dermal skin layers.

III Flavonoid Formulations of the Invention

The subject invention includes multiple ways to formulate flavonoids allowing a wide variety of applications. As used herein, the term "pharmaceutical composition" or "pharmaceutical formulation" shall mean a composition wherein the components of the composition or formulation are of pharmaceutical grade.

Table II lists a variety of dosage types and forms that can serve as a means for delivering the subject flavonoid formulations.

TABLE II

DOSAGE TYPES & FORMS

| TYPE | FORMS |
|---|---|
| ORAL | Pill, Tablet, Capsule, Thin film, Liquid solution or suspension, Powder or liquid or solid crystals, |
| INHALATION | Aerosol, Inhaler, Nebulizer, Smoking, Vaporizer |
| PARENTERAL INJECTION | Intradermal, Intramuscular, Intraosseous, Intraperitoneal, Intravenous, Subcutaneous |
| TOPICAL | Cream, Gel, Liniment or Balm, Lotion, Ear drops, Eye drops, Skin patch (transdermal) |
| SUPPOSITORY | Rectal (e.g., enema), Vaginal (e.g., douche, pessary, etc.) |

The formulations can conveniently be presented in unit dosage form, and can be prepared by methods known in the art of pharmacy. The formulations can be for immediate, or slow or controlled release of the diffusion enhancing compound. The advantages of a sustained release system (also known as time release, controlled release, etc.) are that dosing frequency can decrease and the systemic drug concentrations are steadier for a longer duration as compared to other formulations of the same drug. Appropriate dosages of the compositions of the invention will depend on the metabolism of the given compound, and the severity of the condition being treated.

A. Microparticulate Flavonoid Formulations

Many flavonoids including apigenin and luteolin are practically insoluble in water and almost all solvents suitable for pharmaceutical, cosmetic, and food additive formulations. It has been shown that the methods utilized in the formation of hydrated flavonoids result in the formation of highly dispersed microparticulate colloidal suspensions which enhance bioavailability.

Topical Administration

Disclosed herein are methods for formulating flavonoids into topical application formulations, including methods for dispersed fine microparticulates of flavonoids within a topical formulation.

Provided herein are protective and therapeutic topical formulations to treat skin, including both human skin and animal skin. Such formulations contain a sufficient amount of micoparticulate flavonoid, (e.g., apigenin and/or luteolin) in a sufficient amount for the intended purpose (e.g., a sufficient amount be delivered into the skin and function as a bioactive agent to prevent and/or treat skin cancer). The specific amount of apigenin and/or luteolin desired can be dependent upon the concentration and type of supplemental ingredients used, the user's skin condition, as well as the severity and extent of the user's skin damage.

The formulation can be a topical composition in the form of a spray, lotion, soap, cream, paste, ointment, emulsion (e.g., water-in-oil emulsion, oil-in-water emulsion, microemulsion, emulsion of nanoparticles), colloid, suspension (e.g., suspension of nanoparticles), powder, gel, foam, anhydrous composition, and so forth, as well as combinations comprising at least one of the foregoing forms. The formulation can, for example, be in any form that enables contact between flavonoid hydrate (and other active ingredients of the topical formulation) and the surface of the skin. See the sections below entitled Vehicles and Carriers, and Additives. As used herein, the term "w/o/w emulsion" means a double emulsion in which oil (O) droplets enclosing water (W) droplets are dispersing in water (W), also called water-in-oil-in-water emulsion. As used herein, the term "o/w emulsion" means an emulsion in which oil (O) droplets dispersing in water (W), also called an oil-in-water emulsion.

Transdermal Administration

Included in the invention are transdermal drug deliveries methodologies including topical formulations containing nanosized particulates of relatively insoluble flavonoids. In vitro skin penetration testing with apigenin nanosized particulates infused within oil in water topical emulsions demonstrated unexpectedly high deposited apigenin concentrations within the epidermal and dermal layers. Typical transdermal formulations for the micoparticulate flavonoids are discussed in Section B below. See also Example 21.

Oral Administration

When the flavonoids are prepared for oral administration, they are generally combined with a pharmaceutically acceptable carrier, diluent or excipient to form a pharmaceutical formulation, or unit dosage form. For oral administration, the flavonoids can be present as a powder, a granular formulation, a solution, a suspension, an emulsion or in a natural or synthetic polymer or resin for ingestion of the active ingredients from a chewing gum.

Orally administered flavonoids can also be formulated for sustained release, e.g., the flavonoids can be coated, microencapsulated, or otherwise placed within a sustained delivery device. The total active ingredients in such formulations comprise from 0.01 to 10% by weight of the formulation.

Pharmaceutical formulations containing flavonoids can be prepared by procedures known in the art using well-known and readily available ingredients. For example, the flavonoids can be formulated with common excipients, diluents, or carriers, and formed into dosage forms such as tablets, capsules, solutions, suspensions, powders, aerosols and the like. All of these dosage forms can be for immediate release, sustained release or enteric coated. These can be either for peroral or sublingual or buccal delivery. Examples of excipients, diluents, and carriers that are suitable for such formulations include fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included.

The compositions of the invention can also contain thickening agents such as cellulose and/or cellulose derivatives. They can also contain gums such as xanthan, guar gum or gum arabic, or alternatively polyethylene glycols, bentones and the like.

For example, tablets or caplets containing the flavonoids can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing flavonoids can contain inactive ingredients such as gelatin, microcrystalline cellulose, glycerin, sodium lauryl sulfate, starch, talc, and titanium dioxide, and the like, as well as liquid vehicles such as polyethylene glycols (PEGs) and vegetable oil. Moreover, enteric-coated caplets or tablets containing flavonoids are designed to resist disintegration in the stomach and dissolve in the more neutral to alkaline environment of the duodenum are typically coated with cellulose acetate derivatives.

The flavonoids can also be formulated as elixirs or solutions for convenient oral administration. The pharmaceutical formulations of the flavonoids can also take the form of an aqueous or anhydrous solution or dispersion, or alternatively the form of an emulsion or suspension.

Parenteral Administration

Typical parenteral formulations for the micoparticulate flavonoids are discussed in Section B below.

Inhalation Administration

The flavonoids can also be administered to the respiratory tract. For administration by inhalation or insufflation, the flavonoid compositions disclosed herein may take the form of a dry powder, for example, a powder mix of the therapeutic agent and a suitable powder base such as lactose or starch. The powder composition can be presented in unit dosage form in, for example, capsules or cartridges, or, e.g., gelatin or blister packs from which the powder may be administered with the aid of an inhalator, insufflator, or a metered-dose inhaler (MDI) or dry powder inhaler (DPI).

The flavonoids can also be administered in an aqueous solution when administered in an aerosol or with a dropper. Thus, other aerosol pharmaceutical formulations can comprise, for example, a physiologically acceptable buffered saline solution containing between about 0.01-10% of the disclosed flavonoid ingredients. Liquid formulations may also contain preservatives such methyl and propyl paraben, benzalkonium chloride etc, buffers such as phosphate and citrate buffers, tonicity adjusters such as mannitol, sodium chloride etc and antioxidants such as ascorbic acid, sodium metabisulfite, sodium thiosulfate etc and colors such as D&C yellow #10, FD&C yellow #6 etc. Dry aerosol in the form of finely divided solid flavonoids particles that are not dissolved or suspended in a liquid are also useful in the practice of the present invention. The flavonoids can be formulated as dusting powders and comprise finely divided particles.

For administration to the upper (nasal) or lower respiratory tract by inhalation, the flavonoids are conveniently delivered from a nebulizer or a pressurized pack or other convenient means of delivering an aerosol spray. Pressurized packs can comprise a suitable propellant such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Products can also be delivered by use of Nebulizers.

For intra-nasal administration, the therapeutic agent can also be administered via nose drops, a liquid spray, such as via a plastic bottle atomizer or metered-dose inhaler. Typical of atomizers are the Mistometer (Wintrop) and the Medihaler (Riker).

Suppository Formulations

Additionally, the flavonoids are well suited to dosage types including rectal and vaginal suppository. The pharmaceutical suppository formulations can comprise hydrophobic bases, for example, cocoa butter, and base produced from vegetable oils; hydrophilic bases, for example, gelatin glycerin, and polyethylene glycols.

B. Solubilized Flavonoid Formulations

Disclosed herein are methods for substantially increasing the solubility concentrations of relatively water insoluble flavonoids within heat stable flavonoid solubilizing compounds to enhanced concentration levels (e. g. up to about 10 wt % at ambient temperatures). The solubilized flavonoid can be added to acceptable topical, subcutaneous, oral, peritoneal, aerosol, and nutraceutical formulations.

Besides polysorbates, other heat stable (i.e. stable up to 200° C. or higher) solubilizing compounds that allow for enhanced solubility concentration levels of flavonoids employing the high temperature methods of this disclose include: hyper branched or dendrimeric polyethylene oxide polymer (including sorbitan polyethylene oxide dendrimer), hyperbranched polyethylene glycol, hyperbranched polypropylene glycol, ethoxylated aliphatic alcohols, polyoxyethylene surfactants, carboxylic esters, polyethylene glycol esters, anhydrosorbitol ester and its ethoxylated derivatives, glycol esters of fatty acids, and fatty amine ethoxylates.

Surfactants

Fatty acid esters of sorbitan (generally referred to as spans) and their ethoxylated derivatives (generally referred to as polysorbates) are perhaps the most commonly used nonionics. Thet can be used alone or in combination (e.g. polysorbate 80 and span 80) to form mixed micelles. The sorbitan esters are insoluble in water, but soluble in most organic solvents (low Hydrophile-Lipophile Balance (HLB) number surfactants). The ethoxylated products are generally soluble in water and have relatively high HLB numbers. These nonionic surfactants could be used alone or in a suitable combination to form mixed micelles of the desired HLB. One of the main advantages of the sorbitan esters and their ethoxylated derivatives is their approval as food additives. They are also used in cosmetics and pharmaceutical preparations.

Nonionic surfactant compounds that are useful for enhanced solubility concentration levels of flavonoids having solubility in water less than 1 mg/ml in water and employing the high temperature methods of this invention include: ethoxylated aliphatic alcohols; polyoxyethylene surfactants; carboxylic esters; polyethylene glycol esters; anhydrosorbitol ester and its ethoxylated derivatives; glycol esters of fatty acids; and fatty amine ethoxylates.

The most common nonionic surfactants are those based on ethylene oxide, referred to as ethoxylated surfactants. Several classes can be distinguished: alcohol ethoxylates, alkyl phenol ethoxylates, fatty acid ethoxylates, monoalkaolamide ethoxylates, sorbitan ester and their ethoxylated derivates, ethoxylates, fatty amine ethoxylates, and ethylene oxide-propylene oxide copolymers (sometimes referred to as polymeric surfactants). Another important class of nonionics is the multihydroxy products such as glycol esters, glycerol (and polyglycerol) esters, glucosides (and polyglucosides) and sucrose esters. Amine oxides and sulphinyl surfactants represent nonionics with a small head group. (M J. Schick (ed.): *Nonionic Surfactants: Physical Chemistry*, Marcel Dekker, New York, 1987)

Polysorbates

Polysorbates are a class of emulsifiers used in some pharmaceuticals and food preparation. They are often used in cosmetics to solubilize essential oils into water-based products. Polysorbates are oily liquids derived from PEG-ylated sorbitan (a derivative of sorbitol) esterified with fatty acids. Surfactants that are esters of plain (non-PEG-ylated) sorbitan with fatty acids are usually referred to by the name Span.

Polysorbate 20 (polyoxyethylene (20) sorbitan monolaurate)

Polysorbate 40 (polyoxyethylene (20) sorbitan monopalmitate)

Polysorbate 60 (polyoxyethylene (20) sorbitan monostearate)

Polysorbate 80 (polyoxyethylene (20) sorbitan monooleate)

The number 20 following the polyoxyethylene part refers to the total number of oxyethylene —($CH_2CH_2O$)— groups found in the molecule. The number following the polysorbate part is related to the type of fatty acid associated with the polyoxyethylene sorbitan part of the molecule. Monolaurate is indicated by 20, monopalmitate is indicated by 60, and monooleate by 80. The same numbering is followed in their Span equivalents (Span 20, Span 40, Span 60 and Span 80).

The invention includes methods for increasing the solubility concentrations of relatively water insoluble flavonoids with polysorbates. As previously noted, many flavonoids and specifically apigenin are relatively insoluble in aqueous solutions thus severely limiting their bioavailability for topical, pharmaceutical and nutraceutical applications.

The subject invention includes a method for increasing the aqueous phase solubility levels of polyphenols by utilizing surfactant compounds, in particular Polysorbates 80, 60, 40 and 20. It should be noted that in this example polysorbates 20, 40 and 60 represent a homologous series of polysorbates with varying saturated fatty acids. The number of carbons in the fatty acid chain increases from 12 (polysorbate 20) to 18 (Polysorbate 60). Polysorbate 80 represents an unsaturated fatty acid with 18 carbon chain length (Oleate). These examples are not all inclusive and one trained in the art should recognize the usefulness of these types of nonionic surfactants with any other fatty acid and also other nonionic surfactants of other classes such as polyoxyethylene alkyl ethers of fatty acids. It should also be noted that either anionic surfactants such as docussate sodium or sodium lauryl sulfate or cationic surfactants such as cetrimide or benzethonium chloride can also be used either alone or in combination with nonionic surfactants. Significant aqueous phase enhancements exceeding more than two orders of magnitude have been achieved for several relatively water insoluble polyphenols.

The novel formulations with high flavonoid concentrations can be utilized for oral, inhalation, topical, peritoneal, suppository and nutraceutical applications. This vehicle is particularly useful for peritoneal infusion for autoimmune disease and cancer. The addition of apigenin PS-80 to beverages (particularly alcohol types) will serve as a means for the oral delivery of low soluble concentrations of beneficial flavonoids.

In an advantageous embodiment, the formulation includes an alcohol such as ethyl alcohol to form a soluble flavonoid solution with a reduced viscosity. Other advantageous solvents to reduce the viscosity level the solubilized flavonoid mixture include small-chain alcohols such as isopropyl and benzyl alcohol and ethoxydiglycol and dimethyl isosorbide.

Topical Administration

Topical administration of solubilized flavonoids is typically done in the form of a lotion, cream, gel, or ointment.

Transdermal Flavonoid Delivery

The methods described for increasing the solubility levels of flavonoids within nonionic surfactant solvents enable the Transdermal Flavonoid Delivery (TFD) into the systemic circulation via permeation at a controlled rate. The subject formulations offer a noninvasive route of drug administration by addressing issues related to the inherently low permeability of skin. The skin is a good barrier to drug penetration. Incorporation of penetration enhancers facilitates the absorption of drugs by altering the barrier property of the stratum corneum. Several nonionic surfactants such as polysorbate 80 in topical, oral, and peritoneal applications are considered to be pharmacologically inert, nontoxic, nonirritating, nonallergic, odorless, compatible with most drug and excipients, and have good solvent properties.

Penetration Enhancers

Different classes of penetration enhancers including alcohols and polyols (ethanol, propylene glycol), surfactants (Tween, Span), fatty acids (Oleic acid), amines and amides (Azone, N-methylpyrrolidone), terpenes (limonene) sulfoxides (dimethylsulfoxide), esters (isopropyl myristate) have been developed over the past two decades (French E, Potton C, Walters K. *Pharmaceutical skin penetration enhancement*. In: Walters K, Hadgraft J, editors. New York: Marcel Dekker; 1993. p. 113-44).

Microemulsions

Another formulation approach aiming to enhance skin penetration is the preparation of microemulsions. Microemulsions consist of water, oil, and surfactant that yield a transparent thermodynamically stable liquid. Properties of microemulsions include optical transparency, thermodynamic stability, and solubility of both hydrophobic and hydrophilic components. Microemulsions are clear, stable, isotropic liquid mixtures of oil, water and surfactant, frequently in combination with a cosurfactant. The aqueous phase may contain salt(s) and/or other ingredients, and the "oil" may actually be a complex mixture of different hydrocarbons and olefins. In contrast to ordinary emulsions, microemulsions form upon simple mixing of the components and do not require the high shear conditions generally used in the formation of ordinary emulsions. The two basic types of microemulsions are direct (oil dispersed in water, o/w) and reversed (water dispersed in oil, w/o).

Penetration enhancement from microemulsions can be due to an increase in drug concentration which provides a large concentration gradient from the vehicle to the skin. The nonionic surfactants solvents containing the enhanced flavonoid concentrations (described herein) are well suited for the preparation of microemulsions for transdermal, oral and peritoneal applications.

In one embodiment, a microemulsion contains apigenin is dissolved in polysorbate 80 together with water and ethyl alcohol as a cosurfactant and an oil phase of isoproyl myristate (IPM). This embodiment has topical applications, due to skin penetration properties, as well as oral, injection and nasal spray applications.

The formulations disclosed in this invention allow enhanced transdermal drug delivery methodologies for flavonoids. Of particular note are the disclosed formulations of relatively water insoluble flavonoids, including apigenin, solubilized in nonionic surfactants mixtures. In vitro skin penetration testing with human and mouse skins demonstrated unexpectedly high apigenin accumulation within the epidermal and dermal layers resulting from the application of the disclosed nonionic surfactant mixtures. See Example 21.

Transdermal Patches

Useful for transdermal drug delivery of the relatively insoluble flavonoids is the use of transdermal patches containing the solubilized flavonoid within the nonionic surfactant diluted with an alcohol such as the relatively volatile ethyl alcohol. The outer nonporous barrier of the patch when applied to the skin serves to reduce the evaporation of the relatively volatile alcohol thereby allowing for the increased penetration and delivery of the flavonoid. Other solvent diluents used in cosmetic and foods applications such as alcohols (i.e., ethyl alcohol, glycols, ethoxydiglycol etc.), esters (dimethyl isosorbide etc.) serve to reduced the viscosities of relatively viscous nonionic surfactant thereby increasing the rate and depth of skin penetration when applied to the skin's surface or contained within transdermal patches. Particularly, useful for dermal patch and transdermal patch are the use of microemulsion formulations of flavonoids. The formulations consist of oil-in-water and water-in-oil type microemulsions.

Transdermal patches can be classified into two types of delivery systems—reservoir based and matrix based. Compositions for both are similar except that membranes are used to control the delivery in the reservoir system. Examples of membranes used include polypropylene, low density polyethylene, ethylene-vinyl acetate co-polymer etc. In matrix based formulations drugs can be dispersed/solubilized in the adhesives. Two commonly used adhesive classes include acrylate and silicone based materials. Examples of pressure sensitive acrylate adhesives include, but are not limited to, the DURO-TAK® series (Henkel, USA). Examples of pressure sensitive silicone adhesives include, but are not limited to, the Bio-PSA® series (Dow Corning, USA). Additional information relating to some specific acrylate and silicone based pressure sensitive adhesives are summarized in Table III.

TABLE III

A SUMMARY OF ACRYATE & SILICONE BASED PRESSURE SENSITIVE ADEHESIVES

| ADHESIVE DESCRIPTION | SOLVENT SYSTEM | POLYMER | NOTES |
| --- | --- | --- | --- |
| DURO-TAK® 87-900A | Ethyl acetate | Acrylic non-curing | Reactive or sensitive API's |
| DURO-TAK® (3)87-2516 | Ethyl acetate Ethanol | Acrylate-vinylacetate; self-curing | Long term wear |
| DURO-TAK® 87-4287 | Ethyl acetate | Acrylate-vinylacetate; non-curing | Long term wear |
| BIO-PSA 7-4202 Silicone adhesive BIO-PSA 7-4302 Silicone adhesive | Ethyl acetate | Trimethylsiloxy silanol endblocked PDMS | Amine-compatible |

Solvents and penetration enhancers known to those skilled in the art can also be included in the compositions. Potential, solvents/enhancers can include but are not limited to fatty acids (oleic acid), esters (isopropyl myristate), alcohols (ethyl and isopropyl) and glycols (propylene glycol, hexylene glycol). Other components can include antioxidants (e.g. BHT and BHA) or chelating agents (e.g. citric acid).

Oral Administration

The formulations of this invention can also be administered orally. For oral administration, the flavonoid compositions disclosed here within can be in the form of pills, capsules, suspensions or solutions. For oral administration, the flavonoid compositions disclosed can be in any orally acceptable dosage for including, but not limited to capsules, emulsions, microemulsions, and aqueous suspensions, solutions, dispersions, microcapsules, pills, powders and granules. Typical oral formulations for the solubilized flavonoids are discussed in Section A above.

Parenteral Administration

The formulations of this invention can also be administered parentally. For parenteral administration, the flavonoid compositions disclosed here within can be in the form of injectable solutions or suspensions, such as saline solutions. The term "parenteral," as used herein includes intravenous, subcutaneous, intramuscular, intrasynovial, intrasternal, intralesional and intracranial injection or infusion techniques. Typical formulations include emulsions and microemulsions. Injectable formulations, including emulsions, frequently consist of mixtures of purified water for injection, organic cosolvents, surfactants, suspending agents, preservatives, antioxidants and pH adjusters. Examples of ingredients illustrating each category are as follows, but not limited to:

Cosolvents

Propylene glycol, ethyl alcohol, glycerin, polyethylene glycols, benzyl alcohol, vegetable oil, soybean oil, safflower oil, cottonseed oil, corn oil, peanut oil, sunflower oil, arachis oil, castor oil, olive oil, ester of a medium or long chain fatty acid such as a mono- di- or triglyceride, ethyl oleate, isopropyl myristate, octanol, polyoxyl hydrogenated castor oil, phospholipids and combinations thereof.

Surfactants

Polyoxyethylene/polyoxypropylene block copolymers, phosphatides, and polysorbates are commonly used as synthetic nonionic surfactants Suspending Agents Polyvinyl pyrrolidone (PVP), sodium carboxymethylcellulose and dextran Preservatives Disodium edetate, sodium benzoate, benzalkonium chloride, benzoic acid methylparaben and propylparaben Antioxidants Ascorbic acid, butylated hydroxytoluene, butylated hydroxyanisole, sodium thiosulfate pH Adjusters Sodium hydroxide, tromethamine, sodium citrate, sodium phosphate dibasic and monobasic, sodium acetate, citric acid, phosphoric acid, acetic acid and phosphoric acid Inhalation Administration The formulations of this invention can also be administered by inhalation means. For inhalation administration, the flavonoid compositions disclosed herein can be in the form of aerosols which deliver the flavonoid ingredients as a suspension of fine liquid droplets in a gas to the mouth or nasal passages. Vaporizer and inhalation devices facilitate in the delivery of the flavonoid ingredients. Typical inhalation formulations for the solubilized flavonoids are discussed in Section A above.

Inhalation Administration

The flavonoids can also be administered to the respiratory tract.

IV—Vehicles and Carriers

In addition to the flavonoids, the formulations comprise a vehicle such as a "pharmaceutically acceptable" or cosmetically or "dermatologically acceptable" carrier/vehicle. A "pharmaceutically acceptable carrier" does not substantially adversely affect the pharmacological activities of the active agent, is not deleterious or unsuitably harmful to the recipient thereof and is non-toxic when administered at dosages sufficient to deliver an effective amount of the active ingredient, and the carrier (diluent, excipient, and/or salt etc.) is compatible with the other ingredients of the formulation. Likewise, a "dermatologically acceptable carrier" has the same qualities.

A dermatologically acceptable carrier typically includes ingredients that are chemically and physically compatible with flavonoids, stable with an adequate shelf life, and that aid in penetration of the active ingredient(s) into the skin (e.g., to the epidermis and/or dermis). Optionally, the dermatological carrier contains ingredients that contribute to the ease of application and have pleasing aesthetic properties (color, scent, feel etc.).

Formulation objectives with respect to the drug delivery profile depend on the intended use of a topical product. For sunscreens, antifungals, and keratolytic formulations, enhanced drug delivery and retention in the stratum corneum (the outer layer of skin) is desired. Conversely, topical formulations that are intended to modify the physiology of the skin require drug deposition in and often through the lower layers of the skin (viable epidermis and dermis).

The vehicle can act, for example, as a diluent, dispersant, and/or carrier for other materials present in the formulation (for example, so as to facilitate their distribution when the composition is applied to the skin). Some exemplary vehicles include: organic constituents (such as alcohols, oils, and the like), aqueous based solvents (e.g., those which can dissolve or disperse the active flavone ingredients, e.g., at concentrations that are suitable for use in the therapeutic treatment).

More specifically, the vehicle(s) can include ethanol, isopropanol, benzyl alcohol, glycol (e.g., polyethylene glycols, propylene glycol, ethoxydiglycol, and so forth), oils (such as grapeseed, jojoba, coconut, sesame, mineral etc.), glycerol, fatty acid esters, dimethyl isosorbide, as well as combinations comprising at least one of the foregoing carriers. They can be chosen to solubilize or disperse colloidal microparticulates of the active ingredients at the desired concentrations, in other words, an acceptable carrier is a carrier wherein the active ingredients (including the flavonoids and/or hydrated flavonoids) are dissolved and/or dispersed and suspended as microparticulates.

The vehicle, which can be present in the formulation in an amount of less than or equal to 99.99 wt %, specifically, 80 wt % to 99.99 wt %, based upon a total weight of the formulation, can be in any of the various forms of the desired final formulation as discussed above.

Vehicle components in addition to water and oils can also include liquid emollients, solid emollients, solvents, humectants, thickeners, powders, as well as combinations comprising at least one of the foregoing. Exemplary solvents include ethyl alcohol, isopropanol, ethoxydiglycol, and dimethyl isosorbide, and acetone, as the prevention and/or relief of dryness, and/or for the protection of the skin, such as stearyl alcohol, cetyl alcohol, acetylated lanolin alcohols, stearic acid, isobutyl palmitate, isocetyl stearate, cetyl palmitate, isopropyl stearate, butyl stearate, lanolin, cocoa butter, shea butter, oil (e.g., olive oil, sunflower seed oil, avocado oil, mineral oil), petroleum jelly, and myristate (e.g., butyl myristate, isopropyl myristate, myristyl myristate), as well as combinations comprising at least one of the foregoing.

In an embodiment of the invention, the hydrated or solubilized flavonoids are formulated with an enteric coating to release the flavonoids in the intestines. In another embodiment, the hydrated or solubilized flavonoids are formulated with a cyclodextrin (e.g. s alpha, beta or gamma cyclodextrin).

V—Additives

Hyaluronic Acid (HA)

Within the dermal structure, HA functions as a space filling, structure stabilizing, and cell protective molecule with remarkable malleable physical and superb biocompatibility properties. Additionally, HA structures, which have a high level of visoelasticity, serve to preserve a high level of hydration with this skin. A strong correlation exists between the water content in the skin and levels of HA within the dermal tissue. It is well documented that there are significant alterations in HA physical and biological properties as skin ages—particularly in metabolism, content and deterioration in the mechanical properties of the skin. It is believed that the maintaining of a viable HA presence within the skin's intercellular structure contributes to the viability of a healthy skin physical appearance.

In another aspect, it has been well documented that polysaccharide molecules such as HA do degrade as a consequence of enzymatic and oxidative (free radical) mechanisms. Consequently, it is desirable to develop topical formulations that serve to prevent the decomposition of polysaccharides such as HA. To this end, flavonoids such as flavones serve to meet this need via their well-documented anti-hyaludonidase and anti-oxidant properties—thereby serving to maintain the viability of HA desirable functions protecting against the mechanisms which contribute to its breakdown.

Further, the addition of HA to flavonoid particulate formulations serves to inhibit particulate agglomeration by enhancing the zeta potential of the nanoparticles. Additionally, HA enhances the viscosity of topical formulations thereby serving to prevent nano particulate stratification.

Topically, HA has water storing properties, making it beneficial as a swelling agent and lubricant, enabling its incorporation into cosmetics leading to a perceptible and visible improvement of skin condition. In use, it forms a thin transparent visco elastic surface film that helps to preserve the characteristics of youthful and healthy skin: suppleness, elasticity and tone. Increased skin hydration may swell and open up the compact structure of the stratum corneum, leading to an increase in penetration of the active flavonoids ingredients of the topical formulations described herein.

The formulation can further comprise additive(s) so long as the specific additive(s) do not adversely affect the active ingredient(s). Some possible additive(s) that can be used in the various embodiments of the formulation include:

antioxidant(s) (e.g., tocopherol, tocopheryl acetate, butylated hydroxytoluene, sodium metabisulfite, sodium thiosulfate, and propyl gallate), surfactant(s) (e.g., that can reduce the interfacial tension between phases and/or improve stability of the formulation, and/or that can act as emulsifiers, such as glyceryl stearate, stearyl alcohol, cetyl alcohol, stearic acid dimethicone, a silicone (siloxane) surfactant, polysorbates, sodium laureth), skin conditioning agent(s) such as silicone oils, preservative(s) (e.g., methylparaben, propylparaben, benzyl alcohol, benzalkonium chloride etc.), humectants(s) or emollients or moisturizers such as glycerol, polyethylene glycol, glycerin, sorbitol, mineral oil, isopropyl myristate, etc., buffer(s) (such as phosphate buffers, citrate buffers, and acetate buffers, etc.) pH adjusters such as triethanolamine, potassium hydroxide, sodium hydroxide), hydrochloric acid and phosphoric acid etc., gelling agents such as hydroxypropyl ethyl cellulose, hydroxyrthyl cellulose, polyacrylic acid polymers, and poloxamers, etc.

vitamin(s) (e.g., A, B C, D, E, K, etc.), mineral(s), plant extract(s) (e.g., aloe vera, witch hazel, elderflower, cucumber, chamomile, etc.), anti-inflammatory agent(s), emollient(s), moisturizer(s), skin protectant(s), silicone(s), analgesic(s), skin penetration enhancer(s), such as propylene glycol, transcutol, isopropyl myristate, colorant(s) such as yellow no. 5, fragrance(s) (or perfume), wax(es) (e.g., beeswax, paraffin wax, etc.), propellant(s) (e.g., compressed air, hydrocarbons (such as propane, butane, isobutene, etc.), sunscreen ingredient(s) (e.g., inorganic and/or organic sunscreens, such as titanium oxides, zinc oxides, avobenzone, oxybenzone, homosalate, octocrylene octinoxate etc.), or a combination comprising at least two of the forgoing.

The formulation can contain 0.01 wt % to 20 wt % sunscreen ingredient(s), specifically, 0.1 wt % to about 10 wt %, and more specifically, 0.5 wt % to 5 wt % based upon a total weight of the formulation. For skin products, those vehicles that are fat-soluble, i.e., those which can effectively penetrate skin layers and deliver the hydrated flavone(s) to the lipid-rich layers of the skin.

The flavonoid can be loaded into a formulation by adding it into an oil/water ("o/w") and/or water/oil/water ("w/o/w") emulsion, which can comprise dispersant(s), emulsifiers, surfactants, and the like.

The formulation containing dispersed and/or solubilized flavone(s) and/or hydrated flavone(s) in an admixture colloidal form can be added to a vehicle together with the oxides of titanium and zinc such that the flavone hydrates will preferentially be absorbed within the user's skin while the phase containing the zinc and titanium oxides will not be absorbed but will form a protective UV film barrier external to the surface of the skin.

It is noted that, while the vehicle for the flavone(s) and/or hydrated flavone(s) can comprise a relatively simple solvent or dispersant (such as oils and organic alcohols), it is generally preferred that the carrier comprise a composition more conducive to topical application, and particularly one which will form a film or layer on the skin to which it is applied so as to localize the application and provide some resistance to perspiration and/or one which aids in delivery to the skin (e.g., to the skin's subsurface layers) and penetration of the active ingredients into the lipid layers of the skin. Many such compositions take the form of lotions, creams, sprays and gels. Typical compositions include lotions containing water and/or alcohols, emollients (such as hydrocarbon oils, hydrocarbon waxes, silicone oils, vegetable fats and/or oils, animal fats and/or oils, marine fats and/or oils, glyceride derivatives, fatty acids, fatty acid esters, alcohols (e.g., polyhydric alcohols, alcohol ethers), lanolin (including derivatives), esters (e.g., polyhydric esters, wax esters), sterols, phospholipids, as well as combinations comprising at least one of the foregoing), and generally also emulsifiers (nonionic, cationic or anionic). These same general ingredients can be formulated into a cream rather than a lotion, or into gels, by utilization of different proportions of the ingredients and/or by inclusion of thickening agents such as gums or other forms of hydrophilic colloids.

In one embodiment, the formulation comprises the flavonoids in both the dissolved and dispersed (e.g., microparticulate) forms. The dissolved form(s) can penetrate the skin layers to become bioactive while the dispersed hydrates can serve as a reservoir for maintaining a dissolved concentration level as the dissolved hydrates are consumed so as to maintain sustained flavonoid delivery.

A formulation can be prepared using a lecithin-based oil-in-water cream with about 2.0 wt % apigenin and/or hydrated apigenin and about 0.5 wt % ascorbic acid, with about 0.5 wt % tocotrienol acetate and about 0.25 wt % glycolic acid with the balance comprising the vehicle's components, based upon a total weight of the formulation.

In another example, the formulation can be prepared using a lecithin-based oil in water cream, 3.0 wt % with lecithin, about 0.5 wt % ascorbic acid, about 0.5 wt % tocotrienol acetate, about 0.25 wt % glycolic acid, and about a total of 8 wt % of the oxides of zinc and titanium, with the balance comprising the vehicle's components, based upon a total weight of the formulation.

Optionally, the composition can further comprise: (i) an additive selected from the group consisting of surfactants, vitamins, minerals, plant extracts, anti-inflammatory agents, concentrates of plant extracts, emollients, moisturizers, skin protectants, humectants, silicones, skin soothing ingredients, skin penetration enhancers, colorants, perfumes (fragrances), preservatives, pH adjusters, and a combination comprising at least one of the forgoing; and/or (ii) titanium oxide, zinc oxide, or a combination comprising at least one of the forgoing.

Generally, the flavonoid compositions can comprise greater than or equal to 0.01 weight percent (wt %) flavonoid, specifically, greater than or equal to 1 wt %, for example, 0.1 wt % to 10 wt %, specifically, 0.5 wt % to 8 wt %, more specifically, 2 wt % to 5 wt %, based upon a total weight of the composition. The formulation can comprise greater than or equal to 0.01 wt % flavonoid (e.g., 0.01 wt % to 20 wt % flavonoid, specifically, 0.05 wt % to 15 wt % flavonoid, more specifically, 0.1 wt % to 10 wt % flavonoid, yet more specifically 0.5 wt % to 4 wt % flavonoid, and even more specifically, 1 wt % to 2 wt % flavonoid, based upon a total weight of the formulation.

Ranges disclosed herein are inclusive and combinable (e.g., ranges of "up to 25 wt. %, or, more specifically, 0.5 wt. % to 5 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. As used herein, the term "(meth)acrylate" encompasses both acrylate and methacrylate groups.

TABLE IV

EXAMPLES OF FORMULATIONS CONTAINING THE DISCLOSED MICROPARTICULATES AND SOLUBILIZED FLAVONOIDS

| FORMULATION TYPES | TABLE IV - EXAMPLES OF TYPUCALFORMULATIONS CONTAINING THE DISCLOSED FLAVONOIDS |
|---|---|
| CAPSULES | Capsules containing the poorly soluble flavonoids may include the following ingredients: 0.01-10% of the disclosed flavonoid ingredients (microparticulate and/or solubilized flavonoids in nonionic surfactants together with other active ingredients; and 90-99.9% of inactive ingredients including oils, emulsifiers, solvents, saline solutions, powders, preservatives |
| TABLETS | Tablets are usually compressed preparations that contains: 0.01-10% of the disclosed flavonoid ingredients & other active ingredients; 90-99.9% of fillers, disintegrants, lubricants, glidants, and binders; and 0-10% of compounds which insure easy disintegration, disaggregation, and dissolution of the tablet in the stomach or the intestine. |
| Emulsions (LOTIONS, CREAMS), & GELs | An emulsion is a thermodynamically unstable system consisting of at least two immiscible liquid phase, one of which is dispersed in the other liquid phase. The system is stabilized by the presence of an emulsifying agent. When the oil phase is dispersed throughout an aqueous continuous phase, the system is referred to as an oil-in-water (o/w) emulsion. When the oil phase serves as the continuous phase, the emulsion is referred to as water-in-oil (w/o) emulsion. Both lotions and creams are emulsions. Creams are thicker than lotions. Gels consist of a solid three-dimensional network of a gelling agent that spans the volume of a liquid medium. The key components include: 0.01-10% of the disclosed flavonoid ingredients & other active ingredients; and 90-99.9% of other ingredients such as emulsifiers (surfactants), humectants, emollients, oils, fatty acids, solvents, stabilizing agents, gelling agents, preservatives, vitamins, penetration enhancers, dyes, fragrances, etc, are commonly added ingredients |
| OINTMENTS | Ointments are homogeneous, viscous semi-solid preparations. They are formulated using hydrophobic, hydrophilic, or water-emulsifying bases to provide preparations that are immiscible, miscible, or emulsifiable with skin secretions. The key components include: 0.01-10% of the disclosed flavonoid ingredients & other active ingredients; and 90-99.9% including the ointment base consisting of paraffins, beeswax, vegetable oils, fatty acids, stabilizers, emulsifiers, humectants, preservatives, fragrances, etc. |
| DERMAL & TRANSDERMAL PATCHES | Dermal & Transdermal Patches include the following key ingredients contained within a porous matrix support: 0.01-10% of the disclosed flavonoid ingredients & other active ingredients; and 90-99.9% including penetrating agents, preservatives, stabilizers, gelling agents, solvents such as short chain alcohols, pH adjusters, saline solutions, etc. |
| INJECTABLES | Injectables include the following key components: 0.01-10% of the disclosed flavonoid ingredients & other active ingredients; and 90-99.9% including preservatives, stabilizers, |

TABLE IV-continued

| EXAMPLES OF FORMULATIONS CONTAINING THE DISCLOSED MICROPARTICULATES AND SOLUBILIZED FLAVONOIDS | |
|---|---|
| FORMULATION TYPES | TABLE IV - EXAMPLES OF TYPUCALFORMULATIONS CONTAINING THE DISCLOSED FLAVONOIDS |
| | solvents such as water and short chain alcohols, buffers, pH adjusters, saline solutions, etc. |
| NASAL Formulations (Solutions, Sprays, gels and ointments) | Nasal sprays may be atomized into a fine aerosol mist to include the following ingredients: 0.01-10% of the disclosed flavonoid ingredients & other active ingredients; and 90-99.9% including vegetable derived oils, saline solutions, solvents, stabilizers, surfactants, buffers, preservatives,, pH adjusters, gelling agents and petrolatum etc. |

Nutraceuticals/Food/Dietary Supplements

The microparticulate and solubilized flavonoid compositions of the disclosed invention can be used for many nutraceutical products such as isolated nutrients, dietary supplements, genetically engineered "designer" food, herbal products, and processed products such as cereals, soups, and beverages. As used herein, a nutraceutical is any nontoxic food extract supplement that has scientifically proven health benefits for both the treatment and prevention of disease.

Medical Foods

Medical foods are formulated to be consumed or administered internally under the supervision of a physician. They are intended for the specific dietary management of a disease or condition for which distinctive nutritional requirements, on the basis of recognized scientific principles, are established by medical evaluation. Medical foods can be ingested through the mouth or through tube feeding. Medical foods are always designed to meet certain nutritional requirements for people diagnosed with specific illnesses. The microparticulate and solubilized flavonoid compositions of the disclosed invention can be used in medical foods.

Cosmetics

The formulations of the subject invention can be used, for example, in many products such as cosmetic and dermatological products, including foundations, sunscreen products, sunless skin tanning products, creams (e.g., moisturizing creams, burn creams, skin benefit creams, night creams, dermatological creams, etc.), serums, skin benefit lotions, softeners, gels, ointments, lipsticks, cleansers, toners, masks, hair products, finger nail products, as well as other cosmetic products or applications.

VI—Methods for Forming Vitamin Flavones

Further disclosed herein are methods for forming vitamin flavones. For example, a method for forming a "vitamin flavone" can comprise heating a vitamin until molten; dissolving a flavone in the molten vitamin to form the vitamin flavone liquid mixture; and cooling the vitamin flavone liquid mixture to form a homogeneous solid mixture. In the various embodiments, (i) the flavone can be selected from the group consisting of apigenin, hydrated apigenin, luteolin, hydrated luteolin, and a combination comprising at least one of the foregoing; and/or (ii) the vitamin can be selected from the group consisting of Vitamin B3, Vitamin B5, and combinations comprising at least one of the foregoing vitamins; and/or (iii) the flavone can be present in greater than or equal to 0.1 wt %, specifically, greater than or equal to 25 wt %, more specifically, greater than or equal to 25 wt %, and yet more specifically, greater than or equal to 50 wt %, based upon a total weight of the vitamin flavone.

In one embodiment, a method for the forming a vitamin flavone, can comprise: heating a vitamin until molten, dissolving a flavone in the molten vitamin to form the vitamin flavone, and cooling the vitamin flavone.

Tocotrienols are members of the vitamin E family. An essential nutrient for the body, vitamin E is made up of four tocopherols (alpha, beta, gamma, delta) and four tocotrienols (alpha, beta, gamma, delta).

In many embodiments utilizing tocotrienol in the composition, the tocotrienol is isolated from natural sources and added to the formulation as a tocotrienol-enriched vitamin E preparation. However, synthetic preparations may also be employed as well as mixtures of natural and synthetic vitamin E. Useful tocotrienols are natural products isolated, for example, from wheat germ oil, bran, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. Tocotrienols containing essentially no tocopherol are used in some embodiments.

The combination of tocotrienol and/or tocotrienol-enriched vitamin E preparations in a vehicle with flavone(s) and/or hydrated flavone(s) is especially advantageous because the flavone hydrate(s) (e.g., apigenin and apigenin derivates) augment the efficacy of the other ingredients in the formulation. It is believed that the unsaturated side-chain in tocotrienols enables them to penetrate tissues with saturated fatty layers more efficiently, making them potentially more useful for cosmetic products. Further, the phenol and hydroxy components of tocotrienol contribute to solubilizing the flavone. The combination of two or more active ingredients readily solubilizes in the lipid-rich layers of the skin and scavenges free radicals generated by ultraviolet radiation.

The effectiveness of the combination of apigenin and ascorbic acid (vitamin C) and/or ascorbic acid derivatives with tocotrienols and/or alpha-hydroxy acids are unexpectedly effective compared to their use alone, or even compared to use of lipoic acid, and/or ascorbic acid and/or ascorbic acid derivatives alone.

Also disclosed herein are compositions and food supplements formed from the above methods.

VII—Uses of the Compounds and Formulations of the Invention

Flavonoids have multiple therapeutic applications since they are free radical scavengers, anti-oxidants, superoxide anions, UV absorbers, vasodialators, anti-hyaluronidase (inhibits breakdown of hyaluronic acids by inhibiting hyaluronidases), and lipid peroxy radicals. Flavonoid compounds are also known to be effective in strengthening collagen structures. Further, flavonoids have anti-mutagenic, anti-angiogenic, anti-carcinogenic, anti-inflammatory, and antiviral effects. The anti inflammatory effects include inhibition of TNF-alpha, IL-beta, COX-2, protein kinase PKC, iNOS, and T helper cells Th 1 and Th 17. Flavonoids, apigenin in particular, is a stimulator of p53. Researchers have found that apigenin induces reversible, cell-cycle arrests at G1 and G2/M phase of the cell cycle.

Flavonoids alone or in combination with other preventive and/or therapeutic effective drugs, are effective in treating or preventing in mammals, including humans, the most common diseases such as cancer, autoimmune disease, diabetes, ulcer, cardiovascular disease, atherosclerosis, and liver disease. The compounds also have antithrombogenic activity.

The subject invention includes multiple ways to formulate flavonoids allowing a wide variety of applications. The compounds, compositions and formulations of the invention are useful in the prevention of and the treatment of the disorders and diseases discussed below. As used herein, a "therapeutically effective amount" is the dose necessary to have the desired effect. For example in the case of plaque psoriasis, a therapeutically effective amount is that amount which reduces the sizes or severity of the patches or plaques. A "prophylactic amount" is that dose which prevents or reduces the likelihood of a disorder or disease occurring.

Skin Diseases

This disclosure provides methods for making topical formulations containing flavonoids, such as apigenin, at a pharmaceutically meaningful concentration in a dermatologically acceptable pH range. The flavonoids can be in dissolved form or dispersed (e.g., microparticulates) or a combination of both. The topical application formulation can be a composition in the form of a lotion, cream, spray, dermal patch, transdermal patch and so forth, so as to deliver sufficient flavonoid into mammalian (such as human) tissue (e.g., into mammalian keratinous tissue).

Topical Application Amount

A typical topical dose ranges from 1 to 10 mg/cm$^2$, preferably 1 to 5 mg/cm2 and most preferably from 1 to 3 mg/cm$^2$. The dosage varies according to condition and mode of administration The dose used in FDA sunscreen topical testing is 2 mg/cm$^2$ of exposed skin. "*Re: Tentative Final Monograph for OTC Sunscreen*", Food and Drug Administration (US.). Sep. 11, 1998. Retrieved Sep. 25, 2009 Provided one assumes an "average" adult build of height 5 ft 4 in (163 cm) and weight 150 lb (68 kg) with a 32 in (82 cm) waist, that adult wearing a bathing suit covering the groin area should apply 29 g (approximately 1 oz) evenly to the uncovered body area. Considering only the face, this translates to about ¼ to ⅓ of a teaspoon for the average adult face. Larger individuals should scale these quantities accordingly.

In terms of the amount of topical medication that generally should be applied to affected skin, dermatologists refer to the "fingertip unit" as the recommended guidance. One fingertip unit is approximately 500 mg, and recommendations for the number of units needed to cover affected areas are offered. For example, three fingertip units are required to adequately cover psoriasis on the scalp, whereas eight fingertip units are needed for the entire leg and foot. This method provides a means for patients to more accurately dose their topical medications.

Prevention and Treatment of Skin Damage Due to Solar Radiation

Soluble forms of the flavonoid, e.g. apigenin and/or luteolin, can readily penetrated into and be absorbed by the skin to prevent damage (photoaging) or to repair the skin matrix that has been damaged. As shown in Example 21 below, the formulations of the subject invention allow significant skin penetration of the flavonoid.

The low solubility of apigenin and/or luteolin within vehicle of lotions and creams makes formation of such compositions with desired amounts of flavonoid difficult. In one embodiment, the formulation contains a sufficient amount of soluble hydrated flavonoid at a nearly neutral pH to penetrate into the living skin matrix to minimize or eliminate skin tissue damage to protect living skin from damage caused by exposure to UV rays and/or pre-penetrate. The topical formulations can be administered to an individual, preferably by topical application to the skin of the individual, orally (e.g., as a food supplement), etc. The formulations can be administered in an amount effective to prevent UV damage, e.g., to inhibit free radicals, reactive oxygen species, and/or other oxidizing species.

With respect to its anti skin cancer activities, apigenin acts effectively even in very low concentrations, <about 50 μM. Apigenin exhibits antiproliferative and cytotoxic effects by affecting apoptosis and necrosis mechanisms during cell proliferation and angiogenesis that are the major characteristics of a variety of cancer cells including prostrate cancer, breast cancer, lung cancer, leukemia, thyroid cancer and liver cancer, resulting in the inhibition of proliferation of cancer cells.

Mechanism

The primary mechanisms of flavonoids, e.g. apigenin, are believed to be their capability to increase the stability of p53, its effect on inducing both G1 and G2/M cell cycle arrests and its well documented anti-inflammatory, anti-oxidant, nontoxic, and non-mutagenic properties. These cell cycle arrests are fully reversible after removal of apigenin by washing or its diffusion out of the skin.

In light of the fact that apigenin causes both G1 and G2/M cell cycle arrests, the essence of apigenin's chemopreventative activity may be to inhibit cancer initiation and progression by ensuring that sufficient intrinsic and artificially imposed cell cycle checkpoints exist in the presence of DNA damaging and tumor promoting agents. Apigenin and luteolin treatment of skin prior to sunlight exposure may extend the time cells normally arrest in G1 and G2/M in response to DNA damage. These flavones increase the duration of the G1 phase beyond that which occurs in normal cells in response to DNA damage, or alternatively, these flavones retard cells containing an activated oncogene in G1 when otherwise cell cycle progression would continue even in the presence of substantial DNA damage. Hence, the time spent in G1 and G2/M is critical for cells to efficiently repair all DNA mutations, and thus slow or prevent the carcinogenic process.

Since the effects of sunlight damage are cumulative over a lifetime, the tumor suppressor protein p53, which is the most commonly mutated gene in all human and animal cancers, may already be inactivated in some keratinocytes by the time a person uses a topical application of apigenin and/or luteolin. Since the effects of these flavones are p53-dependent on the G1 arrest and p53-independent on G2/M arrest, in instances where keratinocytes already have an inactivated p53 gene, apigenin will bolster the G2/M arrest in these small foci of premalignant cells in order to prevent additional mutations, translocations, and/or chromosome loss during mitosis. In addition, apigenin and/or luteolin may exert its protective effects by scavenging free radicals generated in response to UV-B/A sunlight irradiation.

It is believed that apigenin treatment can enhance the apoptotic response initiated by UVB. Without being bound by theory, it is believed that the chemo-preventive action of apigenin is explained by its ability to enhance UV-induced apoptosis by significantly increasing the stability of p53 which is a prime factor in the skin cancer apoptosis process. Therefore, there is a need to deliver apigenin into the viable epidermis or the whole skin layer at a pharmaceutically meaningful concentration in order to be effective in skin cancer prevention. (Li B.; Birt D. F.; Pharmaceutical Research, Volume 13, Number 11, November 1996, pp. 1710-1715(6))

As disclosed herein, a composition for the topical application containing flavonoids, particularly apigenin and/or luteolin, is useful for the prevention and/or treatment of skin damage arising from exposure to solar radiation (UVA and/or UVB). Apigenin and/or luteolin compositions also augment the efficacy of other ingredients in topical compositions for sunburn prevention and treatment.

In use, the product can be used in single or multiple applications to attain the desired results. In some embodiments, the sunscreen ingredients can be part of the formulation, and/or can be applied as a secondary application such that a film containing the sunscreen ingredients serves to provide additional full spectrum UV radiation protection by blocking or reflecting UV radiation.

Since apigenin and luteolin function intracellularly on the cell cycle, either could be combined with other sunscreen agents that function simply as a barrier on the outside of the cell to absorb UV energy in sunlight. Thus, topical application of apigenin and/or luteolin, reversible cell cycle regulators, represents a useful and novel approach for skin cancer prevention and can be used sequentially or in combination with currently marketed sunscreen lotions.

These hydrated flavones are exceptionally beneficial as additives to topical formulations for their anti-oxidant, anti-inflammatory, UV skin protection and other desirable properties. Thus, topical application of apigenin and luteolin represent a useful and novel approach for skin cancer prevention/treatment and could be used prior to or in combination with currently marketed sunscreen lotions.

Not to be limited by theory, it is believed that the formulations can be employed, for example, to treat or prevent skin cancers caused by exposure to ultraviolet (UV) light or sunlight.

Disclosed herein are compositions containing flavones or topical applications for the prevention and/or treatment of skin cancer and other topical cancers including but not limited to cervical and breast cancer. The composition contains pharmaceutically sufficient amount of apigenin to penetrate into the skin layer, e.g., to increase the stability of p53 to prevent and treat skin and other topical cancers.

It is believed that the UVB photo-protective effects of the antioxidant apigenin and luteolin are significant when applied in distinct mixtures in appropriate vehicles. Flavone(s) and/or hydrated flavone(s) together with other ingredients provide a natural approach to efficiently supporting the body's own defense mechanism in providing protection from sunburn and chronic UV damage. The natural antioxidant properties and anticancer properties of apigenin and/or luteolin combined with mineral pigments provide a synergistic, photo-protective effect to reduce the risk of UV damage and skin cancer. The other natural ingredients including antioxidants such as vitamin E and moisturizes can be added to create a synergy that enhances UV protection and also soothes the skin.

Also disclosed herein are methods of reducing and/or preventing the effects of sun exposure which can comprise: applying a topical formulation comprising a flavonoid and a dermatologically acceptable carrier to permit delivery of the flavonoid components to mammalian keratinous tissue. Optionally, the topical cosmetic composition can be applied a second time, a third time, or more.

Cancer

Three ideal qualities of a cancer chemopreventative agent are: 1) that it is a natural compound present in foods known to be associated with reduced cancer incidence; 2) that it has a known mechanism of action; and 3) that the effects are reversible. It is believed that flavonoids such as apigenin and luteolin satisfy all three criteria.

The compounds and formulations of the invention can be used for cancer prevention as well as cancer treatment. The formulations are useful for the treatment or prevention of skin cancers (including actinic keratosis, melanoma, basal cell carcinoma), ovarian cancer, cervical cancer, prostate cancer, breast cancer, lung cancer, leukemia, thyroid cancer, liver cancer and brain cancer including neuroblastoma.

Methods of Treatment of Other Skin Disorders

The compounds and formulations of the invention are useful for the treatment of psoriasis. Example 19 demonstrates that topical formulations penetrate human skin in a concentration sufficient to be of therapeutic value.

Additional dermatological disorders and related afflictions/conditions that can be treated or prevented by the topical use of the formulations and compositions of this invention include, but are not limited to the following: acne, alopecia, atopic dermatitis/eczema, cutaneous lupus erythematosus, dermal sensitization and irritation, dry skin (xerosis, ichthyosis), fungal infections, and rosacea, contact dermatosis, autoimmune afflictions including psoriasis, and arthritis. The topical administration of apigenin/flavonoids allows excellent bioavailability. Hence, these topical formulations are alternatives to costly and less desirable steroids and cytotoxic drugs.

Methods of Treatment of Other Disorders

The compounds, compositions and formulations of the invention can also be used for the treatment of other autoimmune disease such as lupus, arthritis, allergies and asthma. The bioavailability of dietary plant-derived COX-2 and NF-kB inhibitors, such as apigenin is valuable for suppressing inflammation in lupus and other Th17-mediated diseases like rheumatoid arthritis, Crohn's disease, and psoriasis, and in prevention of inflammation-based tumors overexpressing COX-2 (e.g. colon, breast). Apigenin suppresses lupus by inhibiting autoantigen presentation for expansion of autoreactive Th1 and Th17 cells. The formulations of this invention offer a novel means of delivering apigenin/flavonoids for the treatment of autoimmune indications/diseases The compounds and formulations are also useful for the treatment of neurological and neurodegenerative disorders. Several research studies have provided support for apigenin and luteolin's anti-inflammatory effects and their neuroprotective/disease-modifying properties in various neurodegenerative disorders, including Alzheimer's disease.

In another embodiment, the compounds and compositions of this invention are useful for the treatment of allergic diseases as well as bacterial infections.

Examples of the TNFα related conditions that can be treated, prevented or ameliorated with the hydrated flavonoids of the invention include, but are not limited to, rheumatoid arthritis, juvenile rheumatoid arthritis, osteoarthritis, spondyloarthropaties, inflammatory bowel disease, chronic heart failure, diabetes mellitus, systemic lupus erythematosus, scleroderma, sarcoidosis, polymyositis/dermatomyositis, psoriasis, multiple myeloma, myelodysplastic syndrome, acute myelogenous leukemia, Parkinson's disease, AIDS dementia complex, Alzheimer's disease, depression, sepsis, pyoderma gangrenosum, hematosepsis, septic shock, Behcet's syndrome, graft-versus-host disease, uveitus, Wegener's granulomatosis, Sjogren's syndrome, chronic obstructive pulmonary disease, asthma, acute pancreatitis, periodontal disease, cachexia, cancer, central nervous system injury, viral respiratory disease, and obesity.

Examples of the IL-1β related conditions to be treated, prevented or ameliorated with the hydrated flavonoids of the invention include, but are not limited to, rheumatoid arthritis, hematosepsis, periodontal disease, chronic heart failure, polymyositis/dermatomyositis acute pancreatitis, chronic obstructive pulmonary disease, Alzheimer's disease, osteoarthritis, bacterial infections, multiple myeloma, myelodysplastic syndrome, uveitis, central nervous system injury, viral respiratory disease, asthma, depression, and scleroderma.

Due to the inhibitory activity of flavonoids on IL-4 and IL-13 synthesis, it can be expected that the intake of flavonoids, depending on the quantity and quality, can ameliorate allergic symptoms or prevent the onset of allergic diseases. (*Int Arch Allergy Immunol.* 2004 June; 134(2): 135-40.)

Apigenin possesses anti-inflammatory activity in human periodontal ligament (hPDL) cells and works through a novel mechanism involving the action of heme oxygenase-1 (HO-1) 1. Thus, apigenin has benefits as a host modulatory agent in the prevention and treatment of periodontal disease associated with smoking and dental plaque. (Gil-Saeng Jeong et al; *Anti-inflammatory effects of apigenin on nicotine-and lipopolysaccharide-stimulated human periodontal ligament cells via heme oxygenase*-1, *International Immunopharmacology*, Vol.: 9, November 2009).

In another embodiment, the compounds and formulations of this invention can be useful for promoting hair growth. Research studies teach that the apigenin stimulates hair growth through downregulation of the TGF-beta1 gene.

It should be understood that a wide range of changes and modifications could be made to the embodiments described above. It is therefore intended that the foregoing description illustrates rather than limits this invention, and that it is the following claims, including all equivalents, which define this invention.

EXAMPLES

Example 1—Unprocessed Apigenin Powder

Apigenin powder with a purity of greater than 98% (determined by HPLC) as noted by an accompanying "Certificate of Analysis" was obtained from Actives International (Allendale, N.J.). This highly refined apigenin (with the trade name Viapure Citrus™) is derived via modification of bioflavonoid from grapefruit peels (*Citrus grandis*). All of the pale yellow appearing apigenin powder passed through an 80 mesh (U.S. Standard Sieve Size) which would indicate a maximum apigenin size of about 200 micrometers (μm). This would indicate that an apigenin particle size reduction of about 200 times would result in a particle size of 1,000 nanometers.

Example 2—Apigenin Solubility

Apigenin solubility testing indicated negligible solubility in water, a limited solubility in both acetone and ethanol (less than 2 mg/ml), and a limited solubility in propylene glycol (<1 mg/ml) and greater than 10 mg/ml in ethoxydiglycol. Although dimethylsulfoxide (DMSO) solubility levels as high as greater than >100 mg/ml have been reported in the literature, DMSO which is recognized as a superior skin penetrating agent, is deemed not suitable for use as a topical ingredient.

Example 3—Apigenin Solubility in Alkaline Solutions

Apigenin is soluble in dilute NaOH solutions. However, it has been experimentally determined that sodium hydroxide solutions proved to be a most effective solvent for apigenin as noted in Table VI.

TABLE VI

Apigenin Solubility in NaOH Solutions

| NaOH Molarity - (M) | Apigenin Solubility (mg/ml) |
|---|---|
| 0.75 | >150 |
| 1.015 | >200 |
| 2.0 | >300 |

Similarly, 1 M solutions of potassium hydroxide (KOH) and lithium hydroxide (LiOH) proved to dissolve similar quantities of the pale yellow apigenin powder and did the 1M solution of NaOH.

To form the hydrated apigenin and/or luteolin, apigenin and/or luteolin powders were initially dissolved in solutions of alkaline metal hydroxides. The hydrated apigenin was formed when the alkaline soluble sodium salt of apigenin (contained in water at a pH of greater than 8) was acidified with an acidic agent such as citric acid or hydrochloric acid (HCl) such that a cloudily and snow-like colloidal (gel-like) precipitate started to form. The reaction was completed as the solution pH is lowered to about 5. The gel like precipitate was filtered and thoroughly washed with distilled water to remove dissolved salts. The precipitate was pressed and further exposed to an airflow to further dry the hydrated apigenin product. Hydrated luteolin was formed in a procedure similar to that described for producing hydrated apigenin.

Example 4—Solubility in Alcohols

The hydrated apigenin and luteolin exhibited limited solubility in a variety of alcohol solvents. These findings were decidedly different from the non-hydrated states of apigenin and luteolin that were essentially insoluble in these alcohol solvents. Alcohols showing limited solubility concentration levels include ethoxydiglycol, isopropyl alcohol, propylene glycol, butylene glycol, and glycerin. Also, the solvent dimethyl isosorbide exhibited a limited solubility concentration levels for both the hydrates of apigenin and luteolin. The saturation solubility concentration levels of the hydrated luteolin exceeded those of hydrated apigenin for all the alcohol solvents tested. It is apparent that the luteolin's four hydroxyl groups compared to apigenin's three accounts for these comparative solubility differences.

Example 5—Solubility in Vitamins

Vitamin B5 and B3, which are solids, were melted to determine if they would solubilize apigenin and/or luteolin. Surprisingly, they did. When the molten liquid mixture (Vitamin B3/apigenin and/or Vitamin B5/apigenin) was added to several lotions products (e.g., while vigorously stirring), the resulting additive mixture appeared to be uniformly dispersed within the (carrier) lotions/creams.

Surprisingly, the reaction between nearly 1 mole of Pro-Vitamin B5 (D,L Panthenol commercially available from Lotioncrafters, Olga, Wash.) and 0.75 moles of hydrated apigenin resulted in a brown viscous liquid mixture that was partially water soluble.

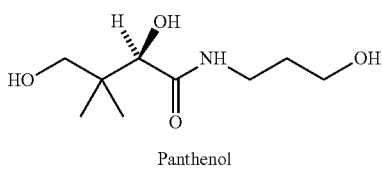

Panthenol

Hydrated apigenin hydrate and apigenin were readily dissolved in molten D,L Panthenol (approximately 65° C.). These mixtures were readily dissolved in a small quantity of alcohols such as ethoxydiglycol or propylene glycol (PG) in order to reduce the viscosity of this mixture. These resulting solutions were added to several available skin moisturizing and/or sunscreen lotions with relative ease and accompanied with a slight elevation of the pH of the lotion. The color of the lotions infused with the molten apigenin/D,L, Panthenol additives resulted in a pale yellow color at about an apigenin concentration of 1.5 wt %, based upon the total weight of the mixture. It should be emphasized that the apigenin and apigenin hydrate solutions in D,L Panthenol were carried out with relative ease. Coincidently, it was established that a 5% wt solution of D,L Panthenol in $H_2O$ was decidedly alkaline with a pH of slightly less than 9.0.

The resulting Apigenin/D,L, Panthenol mixtures were also dissolved in dimethyl isosorbide, glycerin, isopropyl alcohol, and acetone. The Apigenin/D,L Panthenol mixture was insoluble in grape seed and jojoba oils. Also, the pH of a 5 wt % solution of the ApigB5 mixture in $H_2O$ was slightly greater than 8.0. When the Apigenin/D,L Panthenol mixture was acidified with citric acid crystals to a pH of about 6.5, the familiar colloidal and highly dispersed cotton like precipitate (almost oil like consistency) of apigenin hydrate appeared. It appears that Apigenin/D,L Panthenol is an alkaline homogeneous mixture that is readily converted to apigenin hydrate when acidified.

In addition, apigenin and/or hydrated apigenin were readily soluble in molten niacinamide (Vitamin B3). When these molten mixtures, comprising nearly 1 mole of apigenin and 2 moles of niacinamide, were cooled to room temperature, pale yellow/brown solids formed. These solids were soluble in alcohols such as ethoxydiglycol, propylene glycol and isopropyl alcohol. It was noted that the niacinamide fraction of the solid mixture dissolved in water while the hydrated apigenin hydrate was observed to be in a highly dispersed white gel-like (cotton like) form. The pH of this solution was acidic with a pH of approximately 6.0. The apigenin hydrate was nearly completely solubilized when the pH of the solution was elevated to greater than 7.5 with a dilute NaOH solution.

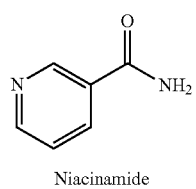

Niacinamide

It should be noted that hydrated apigenin rather than anhydrous apigenin in molten niacinamide was conducted with slightly more control and required slightly reduced molten temperatures.

The addition of molten mixtures of apigenin and apigenin hydrates dissolved within molten Vitamin B3 prior to solidification at about 40° C. to 50° C. to lotions warmed to about 40° C. resulted in uniformly dispersing the apigenin and hydrated apigenin when thoroughly mixed within moisturizing and sunscreen lotions. Further, the addition of the apigenin Vitamin B3 homogenous molten solutions may be added to lotions to provide a pH of 6.5 to 8.0 in order to increase the soluble fraction of the apigenin.

The pH of human skin varies from 4 to 5.6. Sweat and fatty acids secreted from sebum influence the pH of the skin surface. It is suggested that acidity of the skin helps in limiting or preventing the growth of pathogens and other organisms.

Example 6—Solubility of Apigenin in Glycerin

It was further discovered that apigenin was solubilized as either sodium or potassium salt in glycerin concentration levels approaching about 50 mg/ml. Solubilization of apigenin was achieved within an alkaline glycerin solution such that fine crystals of sodium hydroxide and/or potassium hydroxide which did not dissolve in glycerin, dissolved apigenin suspended particles such that a deep yellow solution was observed. Further, sodium and potassium salts of apigenin were dissolved to a much lesser concentration in propylene glycol and to a diminished saturation concentration in a variety of other alcohols.

Example 7—Solubility of Apigenin in Alkaline Solutions and Subsequent Mixing with Topical Carriers The high apigenin solubility levels in alkaline solutions is significant in that it is now conceivable to solubilize apigenin within a pharmaceutically acceptable topical carrier while minimizing sodium and/or other alkali metal ion content. After acidification of the alkaline apigenin formulations, a substantial fraction of apigenin remains dispersed or suspended as fine microparticulates and a very minor fraction was dissolved within the formulation's ingredients.

In one example, 3.3 milliliters (ml) of a 2 molar (M) sodium hydroxide (NaOH) solution containing an apigenin concentration of 300 mg/ml when added to 100 grams of a first topical carrier (Sample No. 1 in Table III) will result in a topical formulation containing nearly 1 wt % dissolved apigenin, based upon total weight of the final mixture. Subsequent neutralization of the NaOH with hydrochloric acid will result in a formulation with a sodium chloride content of only 0.3 wt % or potentially a 0.75 M NaOH solution will result in sodium chloride content of about 0.15 wt %.

In another example, 0.5 ml of NaOH solution containing an apigenin concentration of 200 mg/ml was added to 5 ml of the second topical lotion (Sample No. 2 of Table VII) in an attempt to create a solubilized approximately 2 wt % apigenin concentration. The alkaline formulations resulting from the addition of the NaOH was subsequently neutralized to a slightly acidic pH by the addition of fine crystals of citric acid. Note that the sodium citrate formed with the addition of citric acid will also serve as a preservative in cosmetic formulations.

In another example, 4 ml of ethoxydiglycol solution containing an hydrated apigenin concentration of 75 mg/ml, was added to 96 grams (g) of a third topical lotion (Sample No. 3 of Table VII) in an attempt to create a solubilized fraction of apigenin within a suitable topical formulation. The pH of the third topical lotion with a pH of 5.5 was not altered as a consequence of the addition of the apigenin containing solution.

TABLE VII

Description and Ingredient Listing of Cosmetic Formulations

| Product No. | Name | Description/Ingredients |
|---|---|---|
| 1 | Grins & Giggles (Baby Lotion) (Gerber Products) | An oil in water emulsion containing water, propylene glycol, glyceryl monostearate, myristyl myristate, isopropyl palmitate, cetyl alcohol, strearyl alcohol, carbomer, stearic acid, tetrasodium EDTA, sorbitan stearate, dimethicone, synthetic beeswax, butylparaben, benzyl alcohol, BHT, polysorbate 60, sodium hydroxide, oleic acid, fragrance, tocopheryl acetate, propylparaben, methylparaben, retinyl palmitate, *aloe barbadensis* leaf juice, *chamomile recutita* extract. (A combination of antioxidants, vitamins, surfactants, penetrants, preservatives, etc. with pHs from about 5 to 7 & Apigenin loadings from about 0 to 2.0%) (wt/wt %) |
| 2 | *Aloe* & Chamomile (Advanced Therapy Lotion) (St. Ives) | An oil in water emulsion containing water, glycerin, mineral oil, stearic acid, glycol stearate, stearamide AMP, dimethicone, *aloe barbadensis* leaf juice, *chamomile recutita* extract, sunflower extract, *sambucus nigra* flower extract, *primula veris* extract, cocoa seed butter, glyceryl stearate, cetyl alcohol, triethanolamine, acetylated lanolin alcohol, cetyl acetate, magnesium aluminum stearate, propylene glycol, methylparaben, propylparaben, DMDM hydantoin, disodium EDTA, sorbitol, fragrance, yellow 5, blue 1. (A combination of antioxidants, vitamins, surfactants, penetrants, preservatives, etc. with pHs from about 5 to7 & Apigenin loadings from about 0.5 to 2.0 wt/w %) |
| 3 | Morgan Childs (Hand Lotion with Pure Essential Oils) (Olympic Mountain Products) | An oil in water emulsion containing water, glycerin, mineral oil, stearic acid, glycol stearate, stearamide AMP, dimethicone, *aloe barbadensis* leaf juice, *chamomile recutita* extract, sunflower extract, *sambucus nigra* flower extract, *primula veris* extract, cocoa seed butter, glyceryl stearate, cetyl alcohol, triethanolamine, acetylated lanolin alcohol, cetyl acetate, magnesium aluminum stearate, propylene glycol, methylparaben, propylparaben, DMDM hydantoin, disodium EDTA, sorbitol, fragrance, yellow 5, blue 1. |
| 4 | Soothing *Aloe* Relief (Moisturizer with *Aloe* & Cucumber Extract) (Jergen's Skincare) | An oil in water emulsion containing water, cetearyl alcohol, cetyl esters, ceteareth-20, *aloe* extract, cucumber extract, dimethicone, c12-15 alkyl benzoate, glyceryl dilaurate, mineral oil, ethyhexyl isononoate, cocoa seed butter, mango seed butter, tocopheryl acetate, stearic acid, cetyl alcohol, isopropyl myristate, propylene glycol, carbomer, sodium hydroxide, methylparaben, propylparaben, DMDM hydantoin, fragrance. (A combination of antioxidants, vitamins, surfactants, penetrants, preservatives, etc. with pHs from about 5 to7 & Apigenin loadings from about 0.5 to 2.0 wt/wt %) |

Example 8—Scanning Electron Microscopy (SEM) Images of the Unprocessed Apigenin Powder Scanning Electron Microscopy (SEM) images of the unprocessed apigenin powder were collected to determine the particle shape characteristics. One to two drops of unprocessed samples in water were filtered onto a 0.4 micrometer pore size polycarbonate filter and washed with 20 drops of "water for injection" (WFI). The filters were allowed to dry in a clean hood for a minimum of 24 hours. Samples from each filter were imaged using Scanning Electron Microscopy. FIG. 1 is a typical Scanning Electron Microscopy (SEM) photo detailing the crystal shape of the unprocessed apigenin powder at a magnification of 10,000×.

Example 9—Particle Sizing of Unprocessed Apigenin

Figure 2:
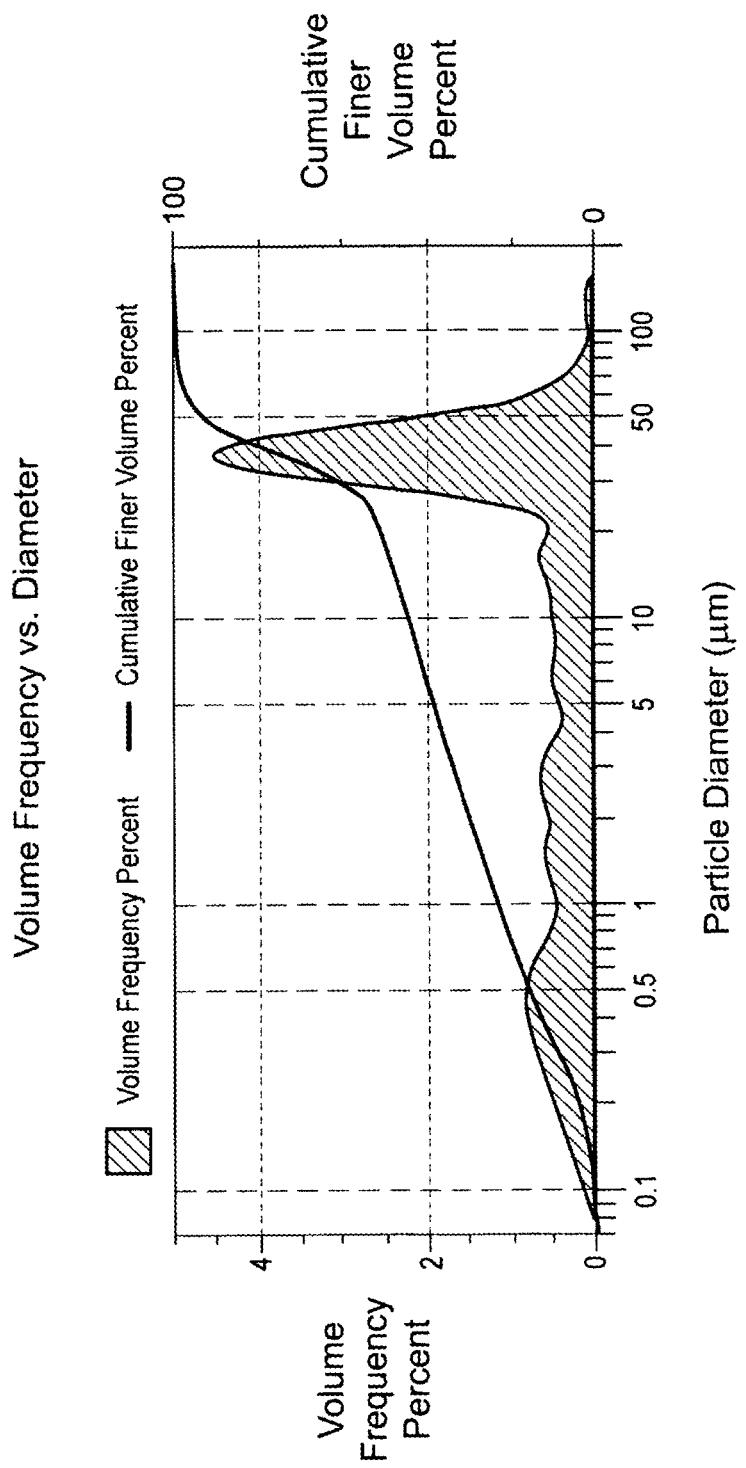
FIG. 2 shows a typical "Volume Frequency" particle distribution plot of the unprocessed apigenin powder.
Figure 3:
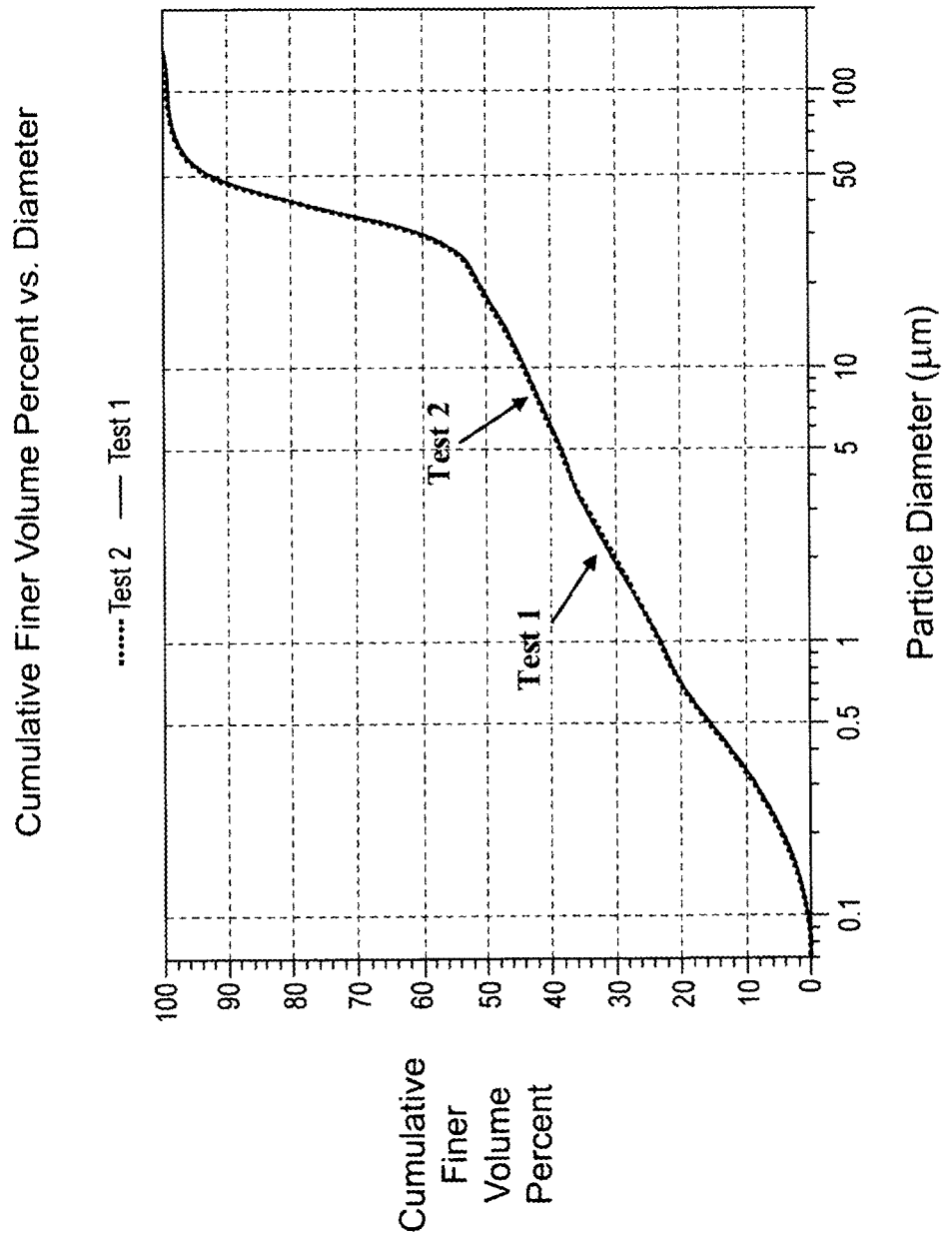
FIG. 3 shows a typical "Cumulative Finer Particle" particle distribution plot of the unprocessed apigenin powder.

The technique of particle sizing by static light scattering, based on Mie theory (which encompasses Fraunhofer theory), was utilized to determine particle size distributions for the unprocessed apigenin samples FIGS. 2 and 3 show typical "Volume Frequency" and "Cumulative Finer Particle" particle distribution plots of the unprocessed apigenin powder. The unprocessed sample has a significant volume of particles <I micron and a very large distribution around 40 microns. These large sized particles have a very narrow range distribution indicating a very uniform particle size. Several of the samples show a significant fraction of the particles below 100 nm.

Example 10—Hydrated Apigenin Morphology

Scanning electron Microscopy (SEM) images of the hydrated apigenin: were collected to determine its particle morphology. The procedure used was similar to that described in Example 8.

Figure 4:
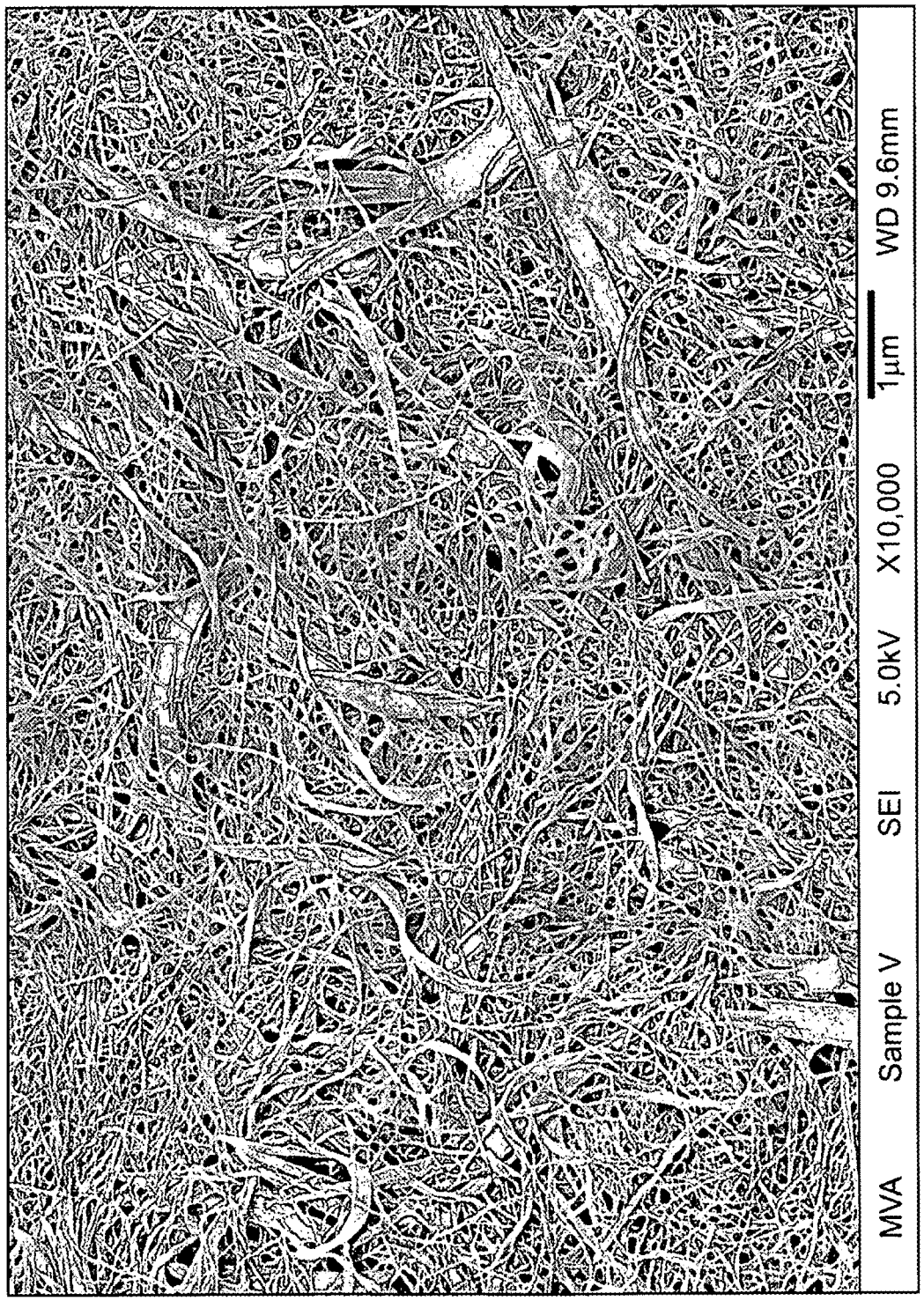
FIG. 4 is a typical Scanning Electron Microscopy (SEM) photo of the hydrated apigenin sample. The morphology exhibited by the unprocessed samples are very different than the morphology exhibited by the typical hydrated apigenin samples as shown in FIG. 1.

FIG. 4 is a typical Scanning Electron Microscopy (SEM) photo of the hydrated apigenin sample. The morphology exhibited by the unprocessed samples are very different than the morphology exhibited by the typical hydrated apigenin samples as shown in FIG. 4. The chemical composition as determined by FTIR and Raman Spectroscopy) could not detect any chemical differences in the unprocessed apigenin and the hydrated apigenin. This suggests that the modification made the formation of hydrated flavonoids has changed the crystal shape and/or crystal habit of the flavones, possibly resulting in a polymorph of the flavones. The fibers had diameters of 30-500 nm with aspect ratios measuring greater than 20.

Example 11—Improved Method of Manufacture

The standard method of making the Aqueous Phase Lotions (APLs) is described below. The HA precipitation conditions which included solution temperature, solution mixing rates during the acidification process, acidification additions rates and pH were duplicated in 3 separate formulations.

The basic APL preparation method to prepare 3 separate 60 ml batches of the Aqueous Phase Lotion (APL) was as follows:

An amount of unprocessed apigenin is weighed which will result in a 1.25 wt % apigenin each of the 60 ml batches.

The unprocessed apigenin is added to 300 ml of D.I. water within a 600 ml beaker and stirred to form solid/liquid slurry.

An amount of a 1M NaOH solution is slowly added to the above slurry while stirring. A sufficient amount is added until all apigenin particulates have been solubilized—thus forming the soluble sodium salt of apigenin.

Ice chips are added to the solubilized apigenin solution to reduce the temperature to about 5° C.

A dilute citric acid solution is prepared which is rapidly added while vigorously stirring the solubilized and alkaline apigenin solution to a pH level of about 4 to 6. During this acidification process, it is noted that a gel-like precipitate forms which becomes decidedly less viscous when the pH<~6.

The gel-like precipitate (hydrated apigenin) is then filtered with a relatively porous filter disk (about 2-microns). Significantly, this precipitation process is rapidly carried out with relative ease such that a clear particle free filtrate is obtained.

Separately, the remaining water soluble constituents of the Aqueous Phase Lotion (APL) are dissolved in water which will result in a concentration within the 30 ml sample of 2% Hyaluronic acid, 2% glycerol, 2% Vitamin B5 and 5% Vitamin B3.

To the above noted solution, hydrated apigenin containing 0.75 grams of apigenin is added to the 30 ml solution. The mixture is then diluted with D.I. water to a level of 60 ml.

The 60 ml solution is then heated to a level of about 120° F. and then sonicated with a QSonics S-4000 sonicator for 1 minute at an amplitude level of 95%. The sonication process is "paused" for 5 seconds after 10 second sonication increments.

The resulting sonicated mixtures were then poured into 20 cc airless dispenser tubes.

Particle Size Distribution Testing

Samples from each of the 3 prepared batches were placed within the 20 cc airless dispensed tubes and labeled as follow:

1. Batch 1: APL 19
2. Batch 2: APL-20
3. Batch 3: APL-21
4. Batch 1: APL-22

APL-19 & APL-22, both from the same Batch were intended as a check on the variability/sensitivity of the Particle Size Distribution (PSD) equipment and analytical procedures employed.

The prepared samples were subject to PSD analysis. Additionally, since the particles were predominately in the submicron range, it was possible to simultaneously measure the Zeta Potential of the nano-sized particulates.

Figure 5:
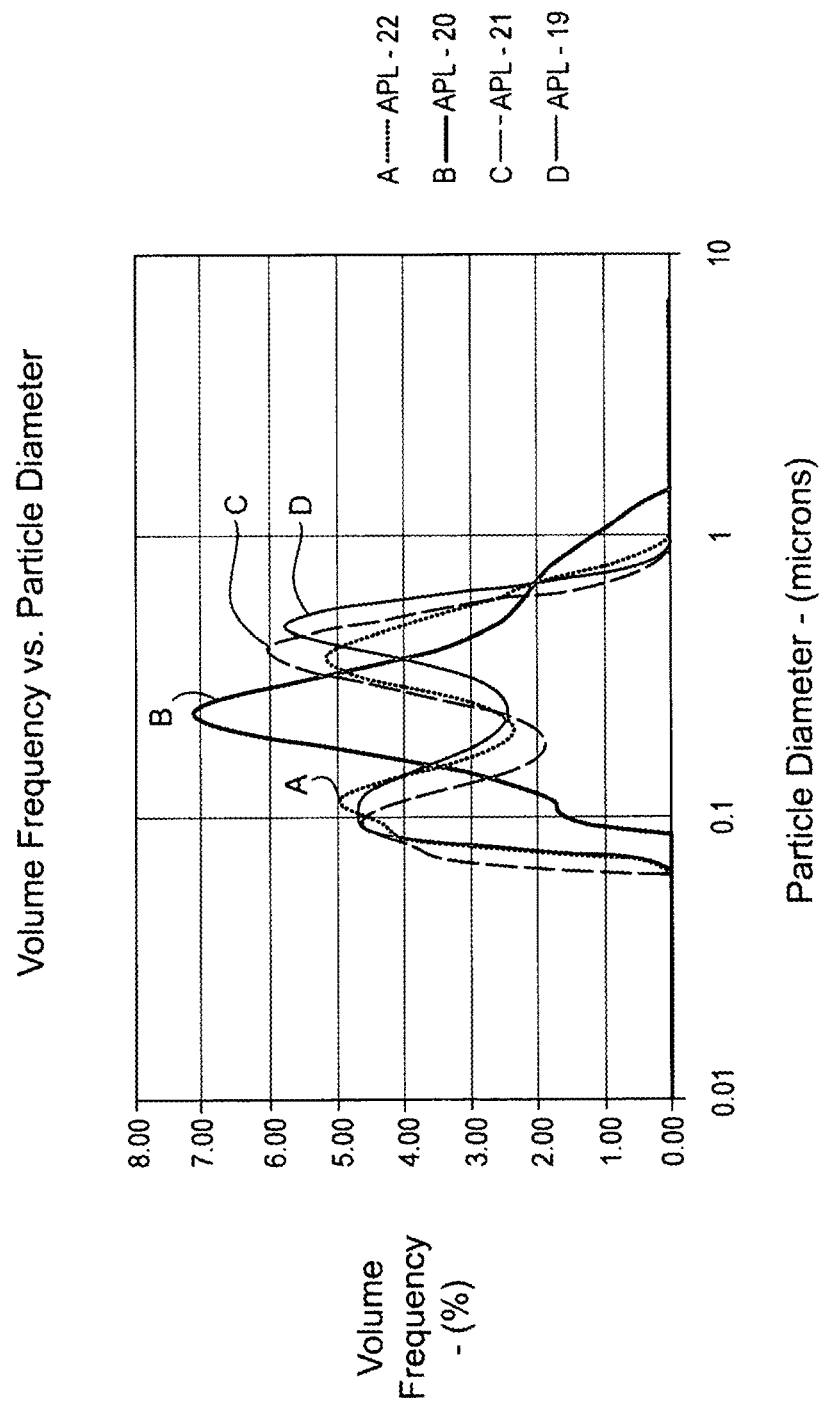
FIGS. 5 & 6 are particle size distribution plots from 3 separately produced "Aqueous Phase Lotion" batches. Nearly all the apigenin particulates are <1 micron.
Figure 6:
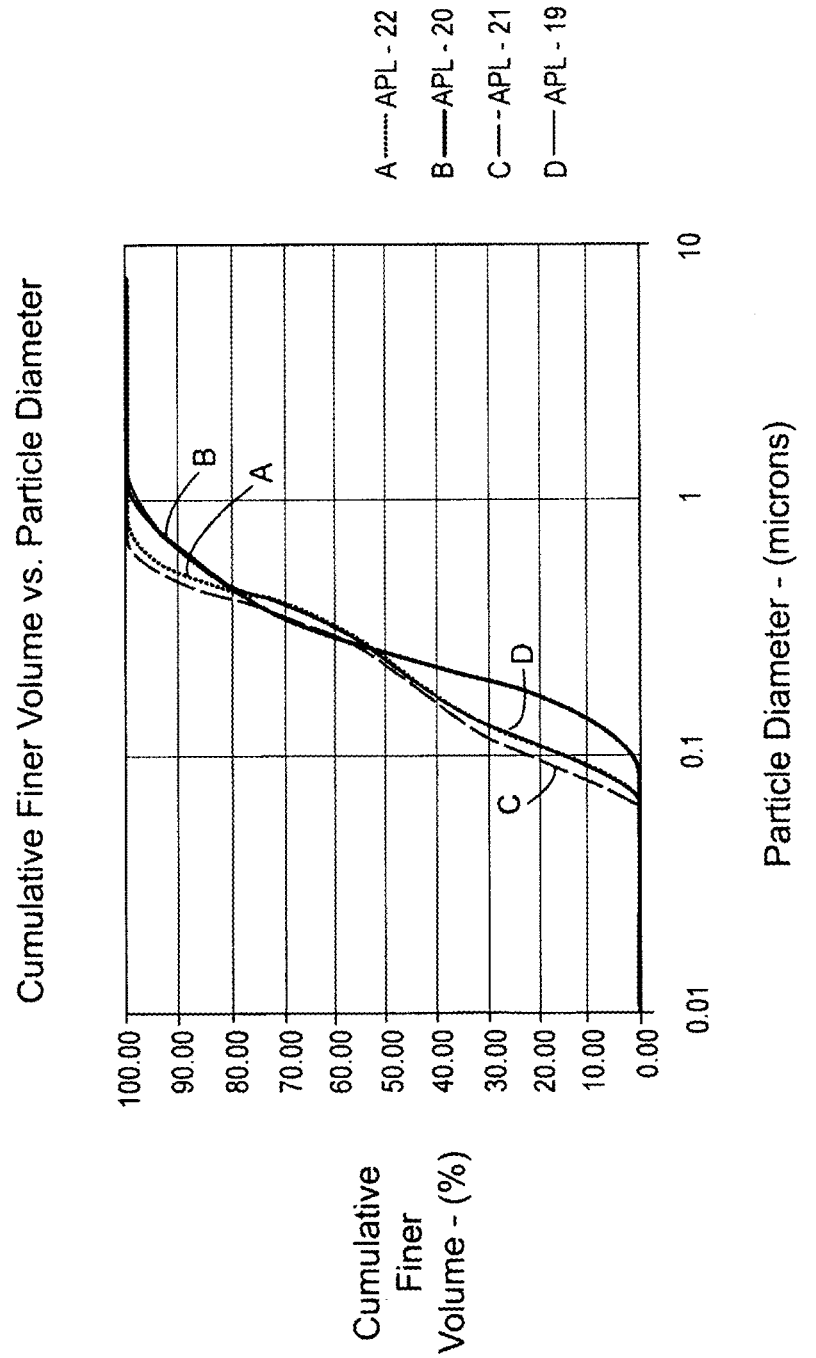

The Particle Size Distributions analytical measurements for the 4 samples, (APL-19 to APL-22), from the 3 separate batches are summarized in FIGS. 5 and 6. APL-19 & APL-22 are from the same batch. As noted in both FIGS. 5 & 6, nearly all the particulates are <1 micron. The samples from the same batch, APL-19 & APL-22, have nearly identical overlays. These similar distributions provide a measure of confidence in the analytical equipment and operator's procedures.

With the exception of sample APL-20, the PSDs noted in FIG. 5 exhibit a bimodal distribution of sizes of ~100 nm & 300-400 nm. The reasons for bimodal distribution separated by about ~250 nm are subject to conjecture. Sample APL-20 has a single peak at about 225 nm—it is believed that the bimodal distributions noted in the other samples had converged to provide a single peak midway between the bimodal distribution peaks.

The "Cumulative Finer Volume" overlays of FIG. 6 show similar particulate distribution agreements between the 4 samples. Notably all samples indicate that ½ of the particulates are <230 nm. With the exception of sample APL-20, ~20% of the particulates are <100 nm. Table VIII summarizes the Zeta Potential results for the 4 samples tested. The samples had been prepared about 5 days prior to the Zeta Potential testing. All the results indicate that the particles have a negative charge at ~40 my. As a rule, particulates with a negative or positive charge exceeding 25 my will tend to repel each other therefore minimizing the potential of agglomerating.

TABLE VIII

ZETA POTENTIAL SUMMARY

| SAMPLE # | ZETA POTENTIAL - (mv) |
|---|---|
| APL - 19 | −42.32 |
| APL - 20 | −41.26 |
| APL - 21 | −39.02 |
| APL - 22 | −39.37 |

Example 12—Other Flavonoid Formulations Employing the Disclosed Methods

Figure 7:
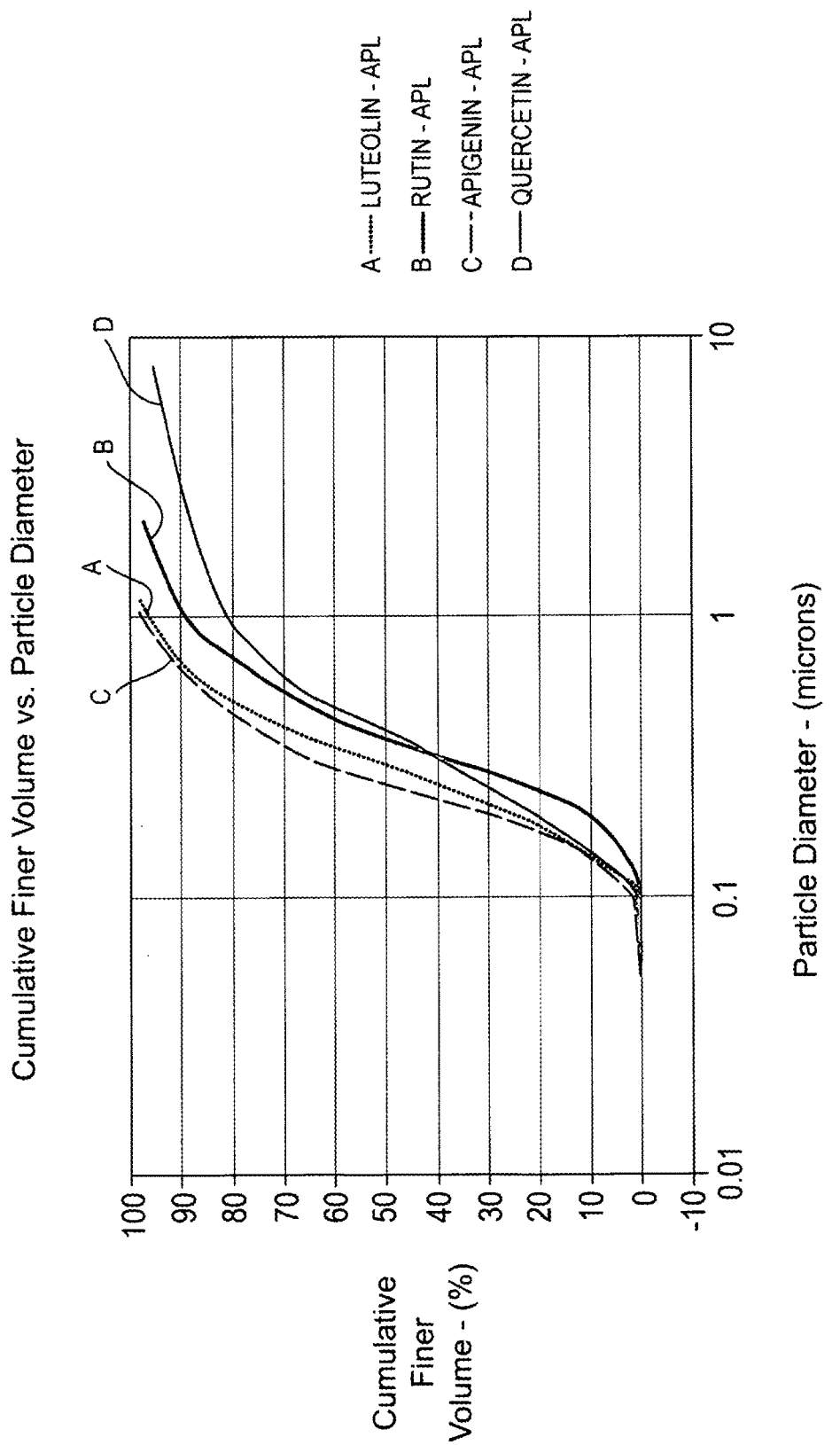
FIG. 7 are plots of "Cumulative Particle Size Distributions" containing 1.25% flavonoid concentrations of apigenin, luteolin, rutin and quercetin within Aqueous Phase Lotions.

Aqueous Phase Lotion (APL) samples of several flavonoids were prepared in a manner outlined in Example 11. Cumulative Particle Size Distributions containing 1.25% flavonoid concentrations of apigenin, luteolin, rutin & quercetin within Aqueous Phase Lotions (APLs) are shown in FIG. 7. The remaining constituents of the APLs include 1% hyaluronic acid, 1% glycerol, 1% vitamin B5, 2.5% vitamin B3, and the balance water. The mean particle sizes are all <400 nm.

Figure 8:
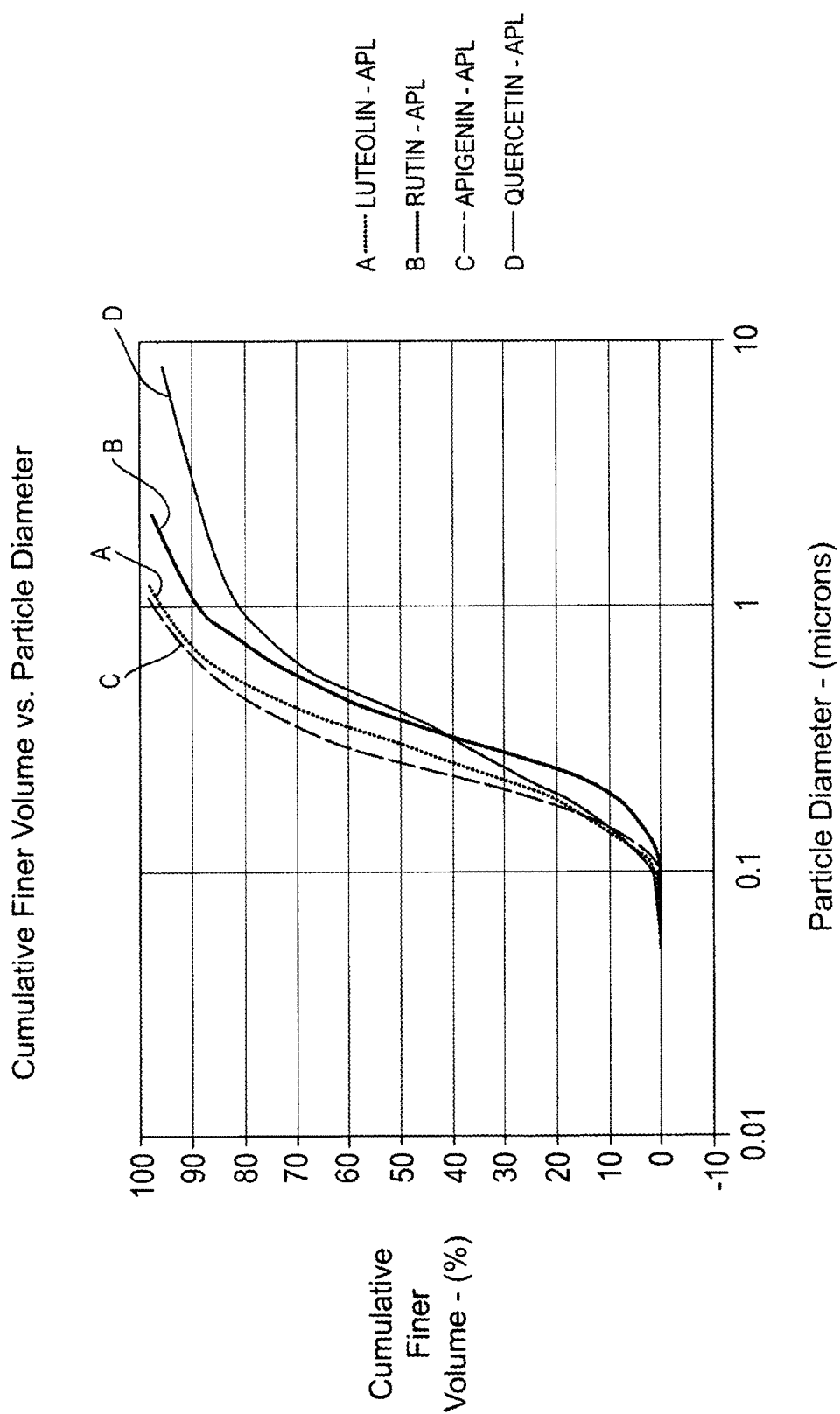
FIG. 8 shows a comparison of the Particle Size Distribution of a 1.25% unprocessed quercetin powder in water compared to a 1.25% "hydrated apigenin" contained within an Aqueous Phase Lotion prepared by the method outlined in Example 2.

FIG. 8 shows a comparison of the Particle Size Distribution of a 1.25% unprocessed quercetin powder in water compared to a 1.25% hydrated apigenin contained within an Aqueous Phase Lotion prepared by the method outlined in Example 2. Significantly, the mean particle size of hydrated quercetin (~400 nm) within an Aqueous Phase Lotion has been reduced by more than an order of magnitude compared to the unprocessed powder.

Table IX contains of qualitative assessment of several hydrated flavonoids contained within an APL when diluted with water to form in a 30 to 1 ratio. The lack of particulate settling after extended time durations provides evidence of the submicron flavonoid particulate content of the Aqueous Phase Lotions.

TABLE IX *

A Qualitative Assessment of "Hydrated Flavonoid" Suspension
Characteristics within an Aqueous Phase Lotion (APL)

| * HYDRATED FLAVONOID | Flavonoid Concentration (%) | Visual Observations after mixing 5 ml of Aqueous Phase Lotion in 150 ml of water | | |
|---|---|---|---|---|
| | | Particulate Settling After 3 hours | Evidence of Flavonoid Solubility | Evidence of Nano Particles |
| APIGENIN | 1.25 | None | Yes (Barely)/ Light Cloudiness | Yes |
| LUTEOLIN | 1.25 | None/ Luteolin Hydrate similar to Apigenin Hydrate | Yes- more so than Apigenin | Yes |
| RESVERATROL | 1.25 | None/Pink paste-like ppt. | Yes | Yes |
| HESPERIDIN | 1.25 | None/Cloudy suspension | A fairly soluble fraction | Yes |
| RUTIN | 1.25 | None | A fairly soluble fraction | Yes |
| QUERCETIN | 1.25 | None | Very Soluble & partially cloudy | Yes |

NOTE:
* Hydrated Flavonoid suspended/dissolved within an Aqueous Phase Lotion" (APL) composed of 1% Hyaluronic Acid (HA), 1% Glycerol, 1% Vitamin B5 (d-Panthenol), 2.5% Vitamin B3 (Niacinamide), balance water.
Note:
Rutin forms a trihydrate; Luteolin forms a dihydrate, Quercetin forms a dihydrate. All are considered nearly insoluble in water; however, "Hydrate Forms" do show slight solubility improvements - in addition to a sizable nano particulate fraction

Example 13—Solubility in Polysorbates

The Apigenin and Polysorbate 80 resulting product is referred to as "A/P80". A/P80 was formed as follows:
  The unprocessed apigenin powder & viscous liquid polysorbate 80 (PS80) were mixed in the ratio from about 5 to 10 wt % of apigenin to 95 to 90 wt % polysorbate 80 and a small quantity of D.I. water and optionally acetone and/or ethyl alcohol in a beaker.
  This mixture was then thoroughly stirred to form a thick paste-like blend.
  The mixture was then slowly heated (e.g. over a gas flame) to relatively high temperatures while stirring. The heating was accompanied by the boiling off of the water and also volatile constituents present in the polysorbate 80. The heating process was conducted with care to avoid the mixture overflowing from the beaker due to foaming resulting from the heating process.
  Upon the removal of the volatiles and heating to temperatures in excess of about 200 to 300° C., a dark brown transparent liquid resulted such that all the solid apigenin is solubilized in the polysorbate 80 mixture.
  Upon cooling to ambient temperatures, a viscous brown clear liquid resulted. The higher the apigenin content—the darker the resulting color)
According to the published solubility results shown in the Table X the solubility of apigenin in water, ethyl alcohol and polysorbate 80 are listed as follows:

TABLE X

Solubility of Apigenin

| SOLVENT | SOLUBILITY | |
|---|---|---|
| | (mg/ml) | (ppm) |
| Water | 0.00135 | 1.35 |
| Ethyl Alcohol | 1.65 | 1,630 |
| Polysorbate 80 | 0.37 | 370 |

The concentration of apigenin in A/P80 was measured by HPLC-MS. Based on the calculated value of 4.05% concentration of apigenin in the viscous A/P80 liquid, the content of apigenin is 40.5 mg/ml or 40,500 ppm.

The following paragraphs list experimental observation attributable to A/PS80.
  The addition of A/PS80 to the standard hydrated apigenin lotions (which contain a substantial concentration of nanoparticulates) contributed to an enhancement in saturation soluble concentration levels. The enhanced solubility level was qualitatively determined via colorimetric testing performed on filtrate liquids passing through a 0.2 micron filter.
  Addition of A/PS80 to Purell (the widely used bactericidal fluid) resulted in an appreciable apigenin soluble level attributable to the high ethyl alcohol content of Purell. The soluble apigenin levels achieved with polysorbate 80 were significantly greater than both hydrated apigenin and unprocessed apigenin.
  Experiments where A/PS80 was added to Purell followed by the application of the apigenin lotion of Example 11 worked quite well. The idea was to take advantage of ethyl alcohol's favorable penetrating and solubility properties (note that ethyl alcohol will evaporate shortly after application which will tend to dry out the skin) followed by the application of our apigenin formation to assist in skin re-hydration.

The concentrations of apigenin in weight % for selected solvents as determined by LCMS (Liquid Chromatography-Mass Spectroscopy) shown in Table XI.

TABLE XI

APIGENIN ANALYTICAL SUMMARY
IN SELECTED SOLVENTS

| SAMPLE DESCRIPTION | SOLUBLE APIGENIN CONCENTRATION (% Wt/Wt) - (mg/ml) |
|---|---|
| Apigenin/PS80 added to Purell Lotion | 0.52% - 5.2 mg/ml |
| Apigenin/PS80 added to Ethyl Alcohol Rubbing Solution | 0.91% - 9.1 mg/ml |
| Apigenin/PS80 (Concentrated Stock Solution) | 4.05% - 40.5 mg/ml |

Additional testing verified that essentially there was insignificant decomposition products resulting as a consequence of heating PS80 with apigenin to elevated temperatures approaching ~250-300° C.

Figure 9:
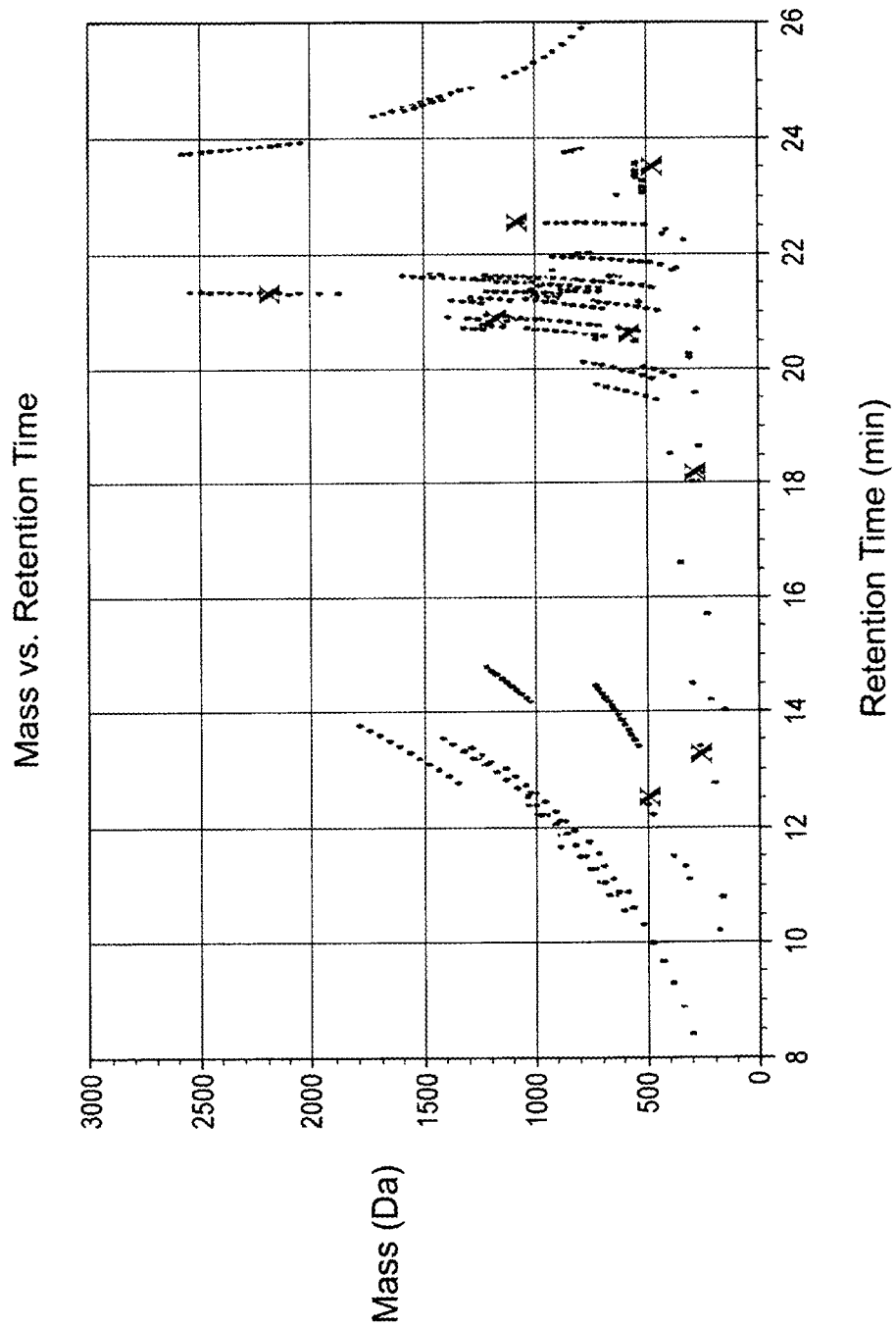
FIG. 9 is a mass spectroscopy plot indicating insignificant chemical composition differences between the unprocessed polysorbate 80 control sample and the thermally treated polysorbate 80 sample.

FIG. 9 shows a statistical analysis of PS 80 prior to heating as compared to the AP80 solution. Insignificant differences were observed between the control sample and the invention sample showing that the surfactant had not degraded. In FIG. 9, each component detected is represented by a dot. PS 80 is a polymer and as such, shows many oligomers. This explains the large number of components or dots on the plot. The Xs are indicative of mass features which are distinct to the AP80 sample statistically. Very few distinct features were observed indicating that the PS 80 did not significantly degrade. The presence of a only a few Xs indicates few differences between the control and invention samples.

Example 14—Additional Flavonoid Polysorbate Formulations

In addition to apigenin, testing with Polysorbate 80 was expanded to include several flavonoid compounds. Table XII includes the chemical and physical property data of the flavonoids selected for solubility testing with Polysorbate 80.

TABLE XII

SUMMARY OF CHEMICAL & PHYSICAL PROPERTIES OF FLAVONOIDS TESTED

| COMPOUND | MW | MP (° C.) | WATER SOLUBILITY (mg/ml) | PARTIAL LISTING OF FLAVONOID SOURCES | APPEARANCE |
|---|---|---|---|---|---|
| APIGENIN | 270 | ~360 | * 0.00002 (>Sol. In alcohol) | Parsley, Thyme, Celery, Chamomile | Yellow Crystalline Powder |
| LUTEOLIN | 286 | ~330 | * 0.38 mg/ml (>Sol. In alcohol) | Celery, Oregano, Thyme. Chamomile | Yellow Powder |
| RESVERATROL | 228 | ~255 | * 0.1 to 0.3 mg/ml 50 mg/ml in alcohol | Red Grapes & Red Wine, Peanuts, Some Berries | White Powder with a slight yellow cast |
| QUERCETIN | 302 | ~315 | * <1 mg/ml | Apples, Tea, Citrus, Broccoli, Berries | Yellow Crystalline Powder |
| HESPERIDIN | 610 | ~260 | * Values cited from 0.05 to 3 mg/ml | Buckwheat, Citrus, Cherries, Grapes | White to Yellow Powder |
| RUTIN | 610 | ~242 | * 0.07 mg/ml | Buckwheat, Citrus, Berries, Tea | Yellow to Green Powder |

* saturation concentrations solubility varied depending on published sources

Table XIII contains a summary of the Polysorbate 80 solubility testing results with a variety of flavonoids.

TABLE XIII

SUMMARY OF FLAVONOID TESTING WITH PS80

| COMPOUND | PS80 SOLUBILITY COMMENTS | SOLUBLE CONC. RANGE (% wt/wt)/ (mg/ml) |
|---|---|---|
| APIGENIN | Solubilzation method previously detailed | 4-6%/ 40-60 mg/ml |
| LUTEOLIN | 1. Same method used as Apigenin. Lower temperature required for solubilization. Much simpler process than apigenin. 2. Also, Luteolin in H2O & PS80 slurry was boiled resulting in solubilizing luteolin but to << extent than process 1. | 1. >8% (80 mg/ml) The upper sol. limit was not determined. 2. Up to ~5% (50 mg/ml) |
| RESVERATROL | 1. Same method as Apigenin. Lower temperatures required for solubiization (perhaps due to the lower MP. Great concept for beverages for a fairly H2O soluble molecule. 2. The H2O boiling method utilized for Luteolin did not dissolve Resveratrol. | 1. >8% (80 mg/ml) The upper sol. limit was not determined. |
| QUERCETIN | 1. Same method used as apigenin. Lower temperature required for solubilization. Much simpler process than apigenin. 2. Also, quercetin in H2O & PS80 slurry was boiled resulting in solubilizing quercetin but to << extent than process. | 1. >7% (80 mg/ml) The upper sol. limit was not determined. |
| HESPERIDEN | 1. Difficulties were encountered in the standard solubilization method. Decomposition of hesperidin occurred resulting in the formation of a gray colored precipitate. However, after filtering out the precipitates, a small quantity dissolved. 2. Add 5% hesperidin in PS80 to water. Boil this mixture o form solubilized Hesperidin. No evidence of the "Anti-Solvent" effect when added to water. | 1. ~<2% (20 mg/ml) 2. ~<1% (<10 mg/ml) |
| RUTIN | 1. Difficulties were encountered in the standard solubilization method. Decomposition of Rutin occurred resulting in the formation of a brown colored precipitate. | 1. ~<1% (<10 mg/ml) 2. ~<0.5% (<15 mg/ml) |

TABLE XIII-continued

SUMMARY OF FLAVONOID TESTING WITH PS80

| COMPOUND | PS80 SOLUBILITY COMMENTS | SOLUBLE CONC. RANGE (% wt/wt)/(mg/ml) |
|---|---|---|
| | However, after filtering out the precipitates, a small quantity dissolved. 2. Add 5% rutin in PS80 to water. Boil this mixture to form solubilized rutin. | |

Example 15—Solubility in Polysorbates Other than Polysorbate 80 Via the Elevated Temperature Processing Method Non-ionic surfactants are extensively used in cosmetics and foods because they are considered to be harmless because they are fatty acid esters of polyalcohol such as sorbitan, sucrose, and glycerin. Consequently, it was decided to evaluate a number of suitable nonionic polysorbate structured surfactants to enhance the saturation solubility concentration via the high temperature processing methods disclosed in Example 13.

Table XIV lists several nonionic surfactants consisting of PEG-ylated sorbitan (a derivative of sorbitol) esterified with fatty acids. All surfactants tested were oily liquids which satisfied the criteria of remaining stable at temperatures >200° C. Similarly, all tested flavonoids including apigenin were selected on the basis of having melting points >200° C.

The flavonoid slurry mixture changes in both particulate solubility and color (a dark brown-red) was observed when temperature levels exceeded 200 to 300° C.

The nonionic surfactants listed in Table XIV are arranged in order of ascending (Hydrophile-Lipophile Balance) HLB values. HLB is an empirical expression for the relationship of the hydrophilic ("water-loving") and hydrophobic ("water-hating") groups of a surfactant. The higher the HLB value, the more water-soluble is the surfactant. The majority are lotions (oil-in-water emulsions) or creams (water-in-oil emulsions). The most common emulsion type, oil-in-water (o/w), often require higher HLB surfactants—preferably 12-16 while water-in-oil emulsions (w/o) require low HLB surfactants—preferable 7-11. Surfactants with an HLB value <10 are oil soluble while those >10 are soluble.

As noted in Table XIV, Span 20 is very suitable for water-in-oil topical formulations while Polysorbate 80 would be most appropriate for solubilizing apigenin in oil-in-water topical formulations.

TABLE XIV

A Summary of Apigenin Solubility in Nonionic Surfactants via the High Temperature Processing Method

| NONIONIC SURFACTANTS | CHEMICAL NAME | Apigenin Solubility (mg/ml) | Apigenin Literature Solubility (mg/ml) | HLB VALUE | USES |
|---|---|---|---|---|---|
| Span 80 | Sorbitan monostearate | ~8 | 0.15 | 4.3 | Foods, beverages, Pharmaceuticals |
| Span 20 | Sorbitan monolaurate | ~10 | 0.17 | 8.6 | Foods, beverages, Pharmaceuticals |
| Polysorbate 60 | Polyoxyethylene (20) sorbitan monostearate | ~15 | — | 14.9 | Foods, beverages, Pharmaceuticals |
| Polysorbate 80 | Polyoxyethylene (20) sorbitan oleate | ~50 | — | 15.0 | Foods, beverages, Pharmaceuticals |
| Polysorbate 20 | Polyoxyethylene (20) sorbitan monolaurate | ~25 | — | 16.7 | Foods, beverages, Pharmaceuticals |
| *Propylene Glycol | — | ~5 | <0.1 | — | Foods, beverages, Pharmaceuticals |

Note:
*Not a surfactant

Example 16—Solubility of Flavonoids in Alkaline Solutions and Subsequent Mixing with Topical Carriers As a consequence of the relatively high solubility of flavonoids in alkaline aqueous solutions (NaOH or KOH), it was discovered that the addition of the flavonoid alkaline solution to a variety of marketed topical compositions which were weakly acidic (i.e., pH from 4.5 to 6.5) while vigorously stirring so as to uniformly disperse the dissolved flavonoids resulted in the nearly complete solubilizing of the flavonoids within several of the marketed topical compositions. The addition of the solubilized alkaline flavonoids to the topical compositions resulted in a highly alkaline mixture.

Subsequent neutralization of these mixtures with the addition of acidic agents such as citric acid or HCl while vigorously stirring reacted with NaOH to form either sodium citrate or sodium chloride, respectively. In some of the topical compositions, the flavonoids remained solubilized. However, in several topical compositions, if the flavonoid solubility limits were exceeded, micro-particulates within the topical composition in addition to a soluble fraction resulted.

Several preparations containing dissolved flavonoid concentrations of about 1.25 wt % were prepared according to the embodiments of the present invention. Table XV contains a summary of several flavonoid preparations. Concentrated solutions containing 0.63 gms of each flavonoid dissolved in 5 ml of a 1.0. M NaOH solution was added to 45 gram quantities of Cetaphil™ Moisturizing Lotion. The alkaline formulations were subsequently neutralized to a slightly acidic pH by the addition of fine crystals of citric acid. Note that the sodium citrate formed with the addition of citric acid will also serve as a preservative in cosmetic formulations Cetaphil™ Moisturizing Lotion was selected as a typical oil in water emulsion whose ingredients include a variety of surfactants, dispersants, pH adjusters, preservatives, emollients, moisturizers, humectants, anti-inflammatory agents, silicones analgesics, polymer thickeners, vitamins, plant extracts, and their combinations. Table XVI contains of a listing of Cetaphil™ ingredients used in the formulations noted in Table VII.

TABLE XV

A Variety of Flavonoid Topical Formulations

| FLAVONOID | Flavonoid Content in 5 ml of 1.0M NaOH added to ~45 gms of Cetaphil Lotion - (gms) | pH after Citric Acid Crystal addition to the Alkaline Flavonoid Cetaphil Lotion | Color of the 1.25 wt % Flavonoid Cetaphil Lotion |
|---|---|---|---|
| APIGENIN | 0.63 | 5.5 | Slight Pale Yellow |
| LUTEOLIN | 0.63 | 5.8 | Pale Yellow |
| HESPERIDIN | 0.63 | 5.2 | Pale Tan |
| RUTIN | 0.63 | 5.6 | Slight Pale Yellow |

TABLE XVI

CETAPHIL ™ MOISTURIZING LOTION

Water Purified, Glycerin, Hydrogenated Polyisobutene, Cetearyl Alcohol, Ceteareth 20, Macadamia Nut Oil, Dimethicone, Tocopheryl Acetate, Steaoxytrimethylsilane, Stearyl Alcohol, Panthenol, Farmesol, Benzyl Alcohol, Phenoxyethanol, Acrylates C10 30 Alkyl Acrylate Crosspolymer, Sodium Hydroxide, Citric Acid Example 17—Sonication Experimental Methods/Procedures The 6 samples listed in Table XVII consisting of about 400 cc and contained within 1 liter HDPE Nalgene wide mouth bottles were prepared for exposure to sonication testing. The samples were subjected to a high level of sonication for 10 minutes using a setting of 100 on the QSonics S-4000 sonicator with a ½" diameter horn. Sonication times and power settings can be adjusted to achieve optimal particulate size reduction profiles.

The ultrasonic electronic generator transforms AC line power to a 20 KHz signal that drives a piezoelectric convertor/transducer. This electrical signal is converted by the transducer to a mechanical vibration due to the characteristics of the internal piezoelectric crystals. The vibration is amplified and transmitted down the length of the horn/probe where the tip longitudinally expands and contracts. The distance the tip travels is dependent on the amplitude selected by the user through the amplitude control knob. For example, with a ½" horn which was employed in the testing, at the 50% amplitude setting, the tip will expand and contract approximately 60 microns (20K times per second). At 100%, there is a tip deflection of approximately 120 μm. In liquid, the rapid vibration of the tip causes cavitation, the formation and violent collapse of microscopic bubbles. The collapse of thousands of cavitation bubbles, releases tremendous energy in the cavitation field. The probe tip diameter dictates the amount of sample that can be effectively processed. Sonicators have been used for a variety of applications which include blending, emulsification, dispersing, homogenization, and deagglomeration, etc processes.

It was readily apparent that cavitational forces resulting from the sonic energy did visually result in the breaking apart of particulate agglomerates as evidence by the creation of particulate suspensions that were significantly less prone to settle out when left undisturbed for extended time periods. The ~200 cc sonicated sample sizes resulted in a temperature elevation of about 30° C. to 40° C. due to the input of 20K vibrations/second of a relatively high input (100% setting) of sonic energy for a suggested 10 minute duration.

As a rule of thumb, elevated processing temperatures can contribute to fine particulate agglomeration (perhaps do to a reduction of the mediums viscosity and the likelihood of enhanced particulate collisions etc.). Many choices are available for limiting the temperature rise of the sonicated solution via the use of a variety of active cooling options (primarily heat transfer coils etc.). To limit the rise in temperature resulting from the input of sonic energy, the beaker containing Sample 6 was immersed within an ice bath. The surrounding ice bath did limit the rise in temperature of these samples to about 20° C. above the ambient temperatures.

In addition to emulsification & homogenization, sonication energy also degasses the samples—a desirable outcome in that the removal of dissolved air contributes to minimizing the potential of the oxidation of the formulation's ingredients. Concerns relating to foaming, which can be an issue with formulations containing surfactants, were alleviated when it was indicated that this would not be a problem providing that the tip of sonicator probe was inserted in the liquid to a depth of about 2". Subsequent testing of the various samples proved that foaming did not occur.

The samples that were sonicated are noted in Table XVIII. The Particle Size Distribution data was obtained on a Malvern Mastersizer analyzer.

The data clearly indicates that the particle size distributions (PSD) of all sonicated samples have been significantly reduced. Table XIII clearly shows that the "Cumulative Volumes" at the 75% & 90% levels have been substantially diminished.

Sonication is a very useful pre and post processing operation that is useful in breaking apart agglomerates that are held together by Van der Waals forces such that improvements in Particle Size Distributions will result.

Example 18—HPH Experimental Methods/Procedures

The samples listed in Tables XIII were prepared for exposure to High Pressure Homogenization (HPH) testing. HPH testing was performed on BEEI's DeBEE 2000 unit.

The DeBEE technology generates intense forces to breakdown droplets and particles to nanometers sizes after only one pass through their system. The DeBEE 2000 intensifiers are hydraulically actuated and microprocessor controlled to deliver a consistent pressure and flow to the DeBEE homogenizing cell. Particle size and particle size distribution are determined by the consistency of flow and pressure applied.

Samples sizes of about 150 cc were flowed through the DeBEE at a rate of about 20-30 cc/min. Following each run, the unit was purged with D.I. water to remove the previous tested residuals and then followed by a purge of the D.I. water in preparation for the next sample to be tested. Following each test, the effluent samples were run through the Malvern Mastersizer analyzer to evaluate the PSD results prior to running the next sample through the HPH unit. Testing on selected samples also included 'Heat Exchanger" (HX) cooling and multiple pass/cycle testing to evaluate the impact of temperature control and multiple HPH cycles on PSD. It is apparent that HX cooling is warranted to achieve finer PSDs while multiple passes had little, if any, impact on the PSD. In general, it is estimated that under the conditions tested, a temperature rise of about 40° C. to 50° C. above ambient was observed for the sample exiting the pressure chamber.

The 9 samples listed in Table XIV were processed through the DeBEE 2000 unit. Four HPH tests were run on Sample 3BEE at internal chamber pressures of 15K psi, 30K psi & 45K psi primarily to determine the impact of pressure on the PSDs and also to determine the impact of HPH processing variables on the apigenin containing samples. As a consequence of the 3 Sample 3 PSD data, it was decided to run the remaining tests at the 45K psi level. As noted in Table III, the PSDs reductions for all samples subjected to the extreme HPH processing conditions were impressive. The uniformity of all samples exposed to 1 pass of HPH yielded PSDs<1 micron at the 90% cumulative volume level. Also, significant is the size reduction of the PSDs of the unprocessed apigenin.

It was readily apparent that cavitational and shearing forces resulting from the HPH energy transfer did result in the breaking apart of particulate agglomerates as evidence by the creation of particulate suspensions that were significantly less prone to settle out when left undisturbed for extended time periods.

The samples that were sonicated were identified by the double asterisks designation (Samples 2 & 5) are also included in Table XV.

The data clearly indicates that the particle size distributions (PSD) of the sonicated and HPH samples have been significantly reduced. For both the sonicated and HPH processed samples "Cumulative Volumes" at the 75% & 90% levels have been substantially diminished. It is quite apparent that the breaking apart of the larger unprocessed particulate agglomerates which is evidenced by a pronounced bimodal PSD distribution results in a cumulative mean PSD at about 350 nanometers.

TABLE XVII

SAMPLE DESCRIPTION

| SAMPLE NUMBER | Unprocessed Apigenin Conc. (%) | "Hydrated Apigenin" Conc. (%) | MEDIUM | pH |
|---|---|---|---|---|
| 1 | 2 | | $H_2O$ | 6.5 |
| 2 | 2 | | $H_2O$ | 7.5 |
| 3 | 2 | | 1% HA* in $H_2O$ | 6.5 |
| 4 | 2 | | 1% HA* in $H_2O$ | 7.5 |
| 5 | | 2 | Lotion** | 6.5 |
| 6 | | 1 | Lotion** | 6.5 |

Note:
*HA is Hyaluronic Acid
**Lotion (Aqueous Phase) consists of 1% HA, 1% Glycerol, 1% Vitamin B5, 2.5% Vitamin B3, Balance $H_2O$

TABLE* XVIII

"SONICATION" TEST RESULTS

| SAMPLE NUMBER | PARTICULATE DIAMETER (microns)/ CUMULATIVE VOLUMES (%) | | | | |
|---|---|---|---|---|---|
| | 10% | 25% | 50% | 75% | 90% |
| 1 | 0.18 | 0.25 | 0.34 | 0.48 | 0.73 |
| 2 | 0.20 | 0.25 | 0.35 | 0.50 | 0.73 |
| 3 | 0.20 | 0.25 | 0.36 | 0.53 | 0.98 |
| 4 | 0.18 | 0.25 | 0.36 | 0.53 | 0.88 |
| 5 | 0.21 | 0.29 | 0.37 | 0.52 | 0.80 |
| 6 | 0.16 | 0.22 | 0.32 | 0.47 | 0.70 |

Note:
*The "Particle Size Distribution" data was obtained on a "Malvern Mastersizer" particle size analyzer

TABLE* XIX

HIGH PRESSURE HOMOGINIZATION (HPH) RESULTS

| HPH SAMPLE NUMBERS | Press. (psi) | HPH Cycles | Short HX Cooling | PARTICLE DIAMETERS (microns)/ CUMULATIVE VOLUMES (%) | | | | |
|---|---|---|---|---|---|---|---|---|
| | | | | 10% | 25% | 50% | 75% | 90% |
| 1 | 45K | 1 | Yes | 0.11 | 0.16 | 0.26 | 0.40 | 0.64 |
| 3 | 15K | 1 | No | 0.18 | 0.29 | 0.36 | 0.57 | 1.17 |
| 3 | 30K | 1 | No | 0.15 | 0.23 | 0.32 | 0.49 | 0.75 |
| 3 | 45K | 1 | No | 0.15 | 0.22 | 0.32 | 0.48 | 0.69 |
| 3 | 45K | 1 | No | 0.18 | 0.25 | 0.35 | 0.50 | 0.73 |
| 5 | 45K | 1 | No | 0.16 | 0.23 | 0.33 | 0.48 | 0.71 |
| 5 | 45K | 1 | No | 0.20 | 0.26 | 0.37 | 0.56 | 0.78 |
| 2** | 45K | 1 | No | 0.17 | 0.25 | 0.33 | 0.47 | 0.63 |
| 5** | 45K | 1 | Yes | 0.17 | 0.24 | 0.32 | 0.44 | 0.60 |

Note:
*The "Particle Size Distribution" data was obtained on a "Malvern Mastersizer"
**These Samples were Pre-Sonicated as noted in Table XIV Example 19—Treatment of Psoriatic Patients with Apigenin Topical Formulation Five psoriatic individuals who were not responsive to Regicide, Methotrexate and several prescription medications experienced significant improvements in their psoriasis conditions as a consequence of applying twice a day, the apigenin containing formulation containing hyaluronic acid. The lotion used was formulated by the acidification of the solubilized sodium salt of apigenin. The oil in water emulation formulation contained 1.5% of the dispersed hydrated apigenin microparticulates. Unexpectedly, all individual who applied the apigenin lotion experienced a gradual improvement in their skin appearance which included psoriasis involvement of the hands, groin, leg and knee. The time required for observing initial objective improvement of these patients varied from 1 to 2 months.

Example 20—In-Situ Method of Manufacture of Formulations

A 100 gm batch containing 1.25 wt % apigenin within an Cetaphil Moisturizing Lotion whose ingredients are listed in Table XII was prepared as follows:
- 90 grams of Cetaphil which has been previously heated to temperatures slightly in excess of 140° F. is added to a 300 cc beaker.
- 1.25 gms of unprocessed apigenin powder as described in Example 1 is then added to the liquid Cetaphil lotion. Optionally, addition ingredients including hyaluronic acid, vitamins etc. can be added to the fluid mixture.
- The ~90 cc fluid solution at the elevated temperature levels (135° F.-150° F.) is then sonicated with a QSonics S-4000 sonicator at an amplitude level of 90% for a total of 10 minutes. The sonication process is paused for 30 seconds after each 1 minute sonication duration.
- Water is then added to the sonicated solution to provide a total solution weight of 100 gms and the resulting solution is sonicated for ~10 seconds at the 90% amplitude level prior to pouring into dispenser containment tubes.

Example 21—In Vitro Percutaneous Absorption of Apigenin from Formulations Using Human Skin and Mouse Skin Potential bioavailability can be assessed using in vitro percutaneous absorption testing. The purpose of this study was to characterize the in vitro percutaneous absorption of apigenin from the disclosed inventive formulations following topical application to excised human skin from elective surgery and fresh mouse skin. The study was conducted using procedures adapted from the FDA and AAPS Report of the Workshop on Principles and Practices of in vitro Percutaneous Penetration Studies: Relevance to Bioavailability and Bioequivalence (Skelly et al., 1987). Human tissue from a single donor and murine tissue was dosed with 5 mg/cm$^2$ of formulation.

An in vitro percutaneous absorption study evaluated permeation and penetration of apigenin from prototype formulations as described in this invention.

The clinically relevant dose of 5 mg/cm$^2$ was applied to dermatomed human abdominal skin from a single donor obtained following elective surgery. The thickness of the tissue ranged from 0.021-0.039 inches (0.533-0.991 mm).

The clinically relevant dose of 5 mg/cm$^2$ was applied to murine tissue. The thickness of tissue ranged from 0.011-0.025 inches (0.279-0.635 mm).

Results

Figure 10:
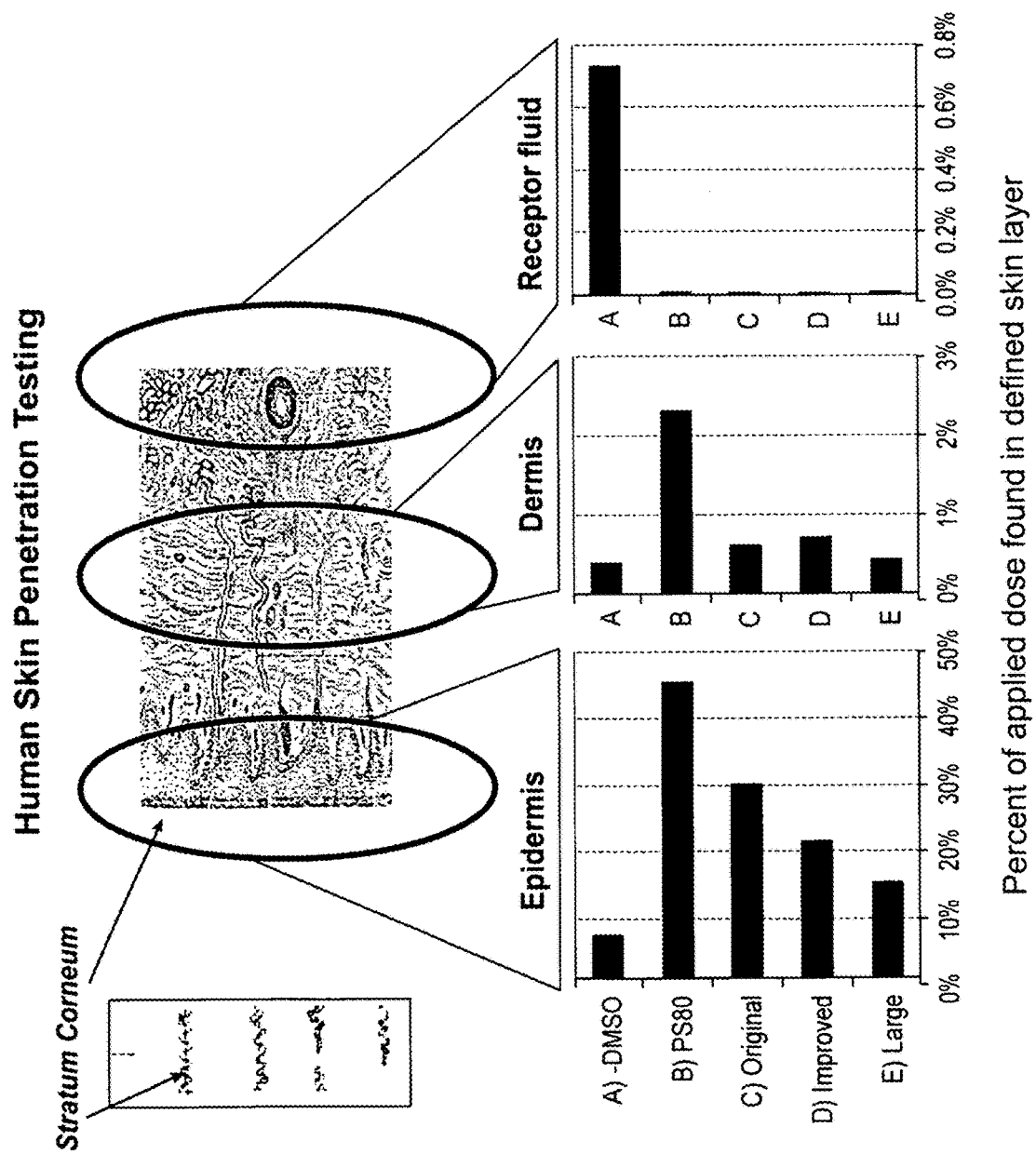
FIG. 10 is a graphical plot illustrating the apigenin content deposited within the epidermal, dermal and receptor fluid segments of human tissues for several applied topical formulations containing 1.5% apigenin concentrations.
Figure 11:
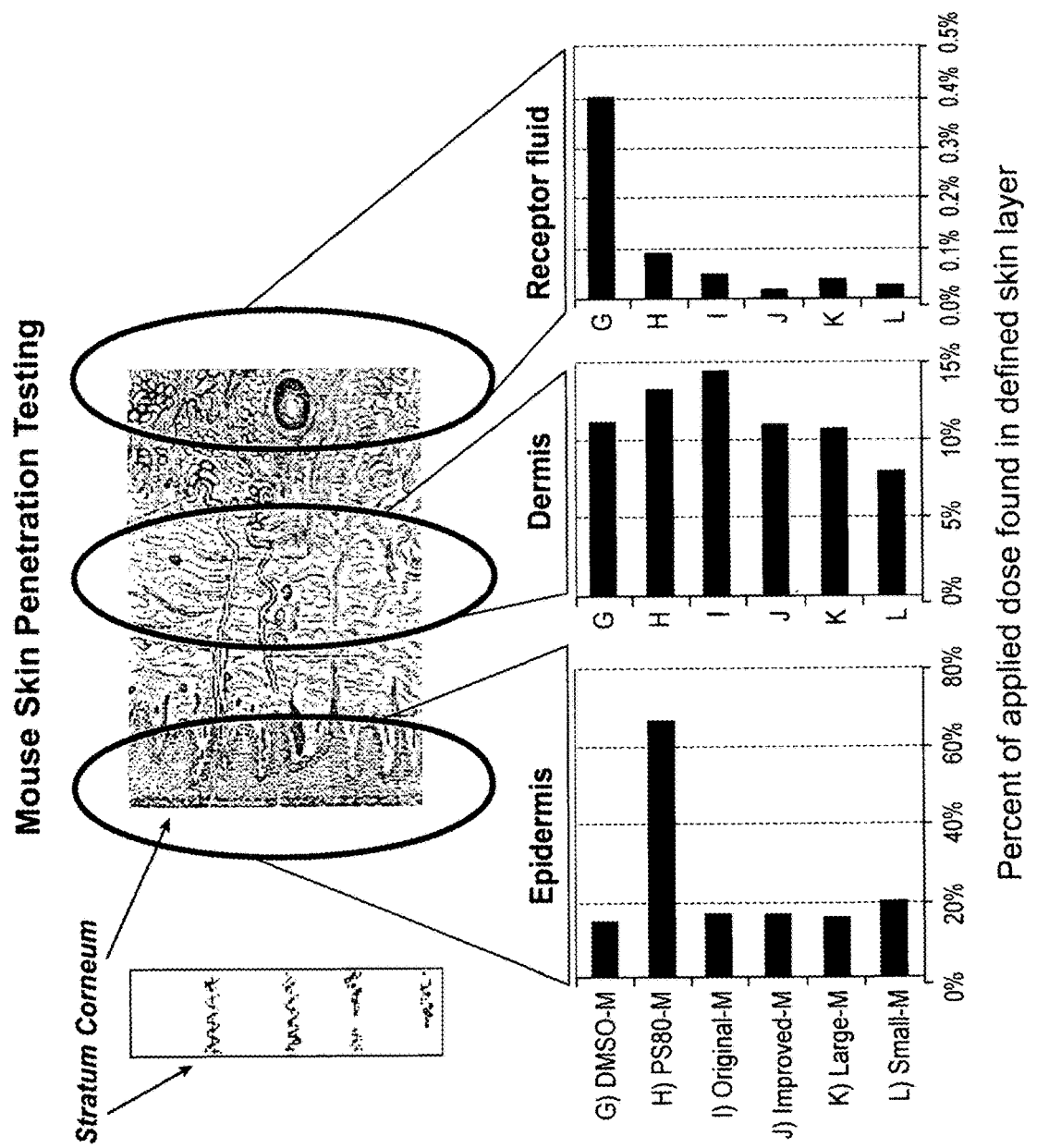
FIG. 11 is a graphical plot illustrating the apigenin content deposited within the epidermal, dermal and receptor fluid segments of murine tissues for several applied topical formulations containing 1.5% apigenin concentrations

FIG. 10 is a graphical illustration of the epidermal, dermal and receptor fluid apigenin profiles for the human tissue with several topical formulations containing 1.5% apigenin concentrations. Similarly, FIG. 11 summarize the epidermal, dermal and receptor fluid apigenin profiles for the human tissue with several topical formulations containing 1.5% apigenin concentrations.

The efficiency of apigenin epidermal deposition (in human tissue) from the prototype formulations ranged from 15.5 to 45.7% of the applied dose of apigenin. The efficiency of apigenin epidermal deposition (in murine tissue) from the prototype formulations ranged from 15.0 to 88.3% of the applied dose of apigenin.

The efficiency of apigenin dermal deposition (in human tissue) from the prototype formulations ranged from 0.446 to 2% of the applied dose of apigenin. The efficiency of apigenin dermal deposition (in murine tissue) from the prototype formulations ranged from 8.0 to 14.4% of the applied dose of apigenin.

The total amount of apigenin delivered from a formulation is dependent upon the concentration of apigenin in the product as well as the efficiency of delivery. Calculated mass of apigenin permeating the human tissue following a dose of 5 mg formulation per square centimeter of skin for 24 hours (receptor phase levels) ranged from 4.04 to 9.88 ng/cm$^2$ of apigenin.

The calculated mass of apigenin epidermal deposition (in human tissue) following a dose of 5 mg formulations per square centimeter of skin for 24 hours (receptor phase levels) ranged from 22,651 to 34,293 ng/cm$^2$ of apigenin.

The calculated mass of apigenin epidermal deposition (in murine tissue) following a dose of 5 mg formulations per square centimeter of skin for 24 hours (receptor phase levels) ranged from 11,232 to 66,209 ng/cm$^2$ of apigenin.

The calculated mass of apigenin dermal deposition (in human tissue) following a dose of 5 mg formulations per square centimeter of skin for 24 hours (receptor phase levels) ranged from 334 to 1,499 ng/cm$^2$ of apigenin.

The calculated mass of apigenin dermal deposition (in murine tissue) following a dose of 5 mg formulations per square centimeter of skin for 24 hours (receptor phase levels) ranged from 6,002 to 10,814 ng/cm$^2$ of apigenin.

The PS80 formulations of the subject invention delivered significant apigenin concentrations to both the epidermal and dermal skin layers.

All documents and references cited above are hereby incorporated by reference in their entirety in this application.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of forming a topical formulation of apigenin comprising:
   mixing apigenin with an alkali metal hydroxide in water to form an alkali metal apigenin salt solution for a first duration of mixing time;
   adding the alkali metal apigenin salt solution to a dermatologically acceptable carrier selected from the group consisting of ethanol, isopropanol, benzyl alcohol, glycol, oils, glycerol, fatty acid esters, dimethyl isosorbide, and combinations thereof,
   after the first step, adjusting a pH of the formulation with an acid to 4 to 8 for a second duration of precipitation time,
   wherein the adjusting the pH step produces apigenin nanofibers having an average size of 50-1000 nanometers and an aspect ratio measuring greater than 20, and
   wherein a ratio of the first duration of mixing time to the second duration of precipitation time is 1:1 to 1:5.

2. A method according to claim 1, wherein the ratio of the first duration of mixing time to the second duration of precipitation time is 1:1 to 1:2.

* * * * *